(12) United States Patent
Sverdlik et al.

(10) Patent No.: US 12,364,501 B2
(45) Date of Patent: Jul. 22, 2025

(54) ULTRASOUND TRANSDUCER AND USES THEREOF

(71) Applicant: Sonivie Ltd., Rosh HaAyin (IL)

(72) Inventors: Ariel Sverdlik, Tel-Aviv (IL); Or Shabtay, Kibbutz Farod (IL)

(73) Assignee: Sonivie Ltd., Rosh HaAyin (IL)

( * ) Notice: Subject to any disclaimer, the term of this patent is extended or adjusted under 35 U.S.C. 154(b) by 0 days.

(21) Appl. No.: 18/235,904

(22) Filed: Aug. 21, 2023

(65) Prior Publication Data

US 2023/0389954 A1 Dec. 7, 2023

Related U.S. Application Data

(60) Continuation of application No. 16/451,087, filed on Jun. 25, 2019, now Pat. No. 11,730,506, which is a
(Continued)

(51) Int. Cl.
*A61B 17/32* (2006.01)
*A61B 17/22* (2006.01)
(Continued)

(52) U.S. Cl.
CPC .. *A61B 17/320068* (2013.01); *A61B 17/2202* (2013.01); *A61M 37/0092* (2013.01);
(Continued)

(58) Field of Classification Search
CPC ........ A61B 17/320068; A61B 17/2202; A61B 2017/00106; A61B 2017/22008;
(Continued)

(56) References Cited

U.S. PATENT DOCUMENTS

| 4,319,580 A | 3/1982 | Colley et al. |
| 5,038,789 A | 8/1991 | Frazin |

(Continued)

FOREIGN PATENT DOCUMENTS

| CA | 2954897 | 11/2016 |
| CN | 1279595 | 1/2001 |

(Continued)

OTHER PUBLICATIONS

Advisory Action Before the Filing of an Appeal Brief Dated Feb. 4, 2019 From the US Patent and Trademark Office Re. U.S. Appl. No. 13/449,539. (6 pages).
(Continued)

*Primary Examiner* — Sanjay Cattungal

(57) ABSTRACT

According to some embodiments there is provided a method for controlling a treatment effect on blood vessel tissue during an ultrasonic treatment, the method comprising positioning an ultrasonic transducer device in the blood vessel lumen; controlling a treatment effect by controlling fluid flow, wherein controlling comprises deploying a fluid restrictor at a location relative to the transducer effective to block at least a portion of fluid flowing upstream, downstream or adjacent the transducer. According to some embodiments there is provided an ultrasonic transducer device sized for placement in a body lumen, and comprising a fluid restrictor effective to block at least a portion of fluid flowing upstream, downstream or adjacent the transducer. In some embodiments, the fluid is blood.

28 Claims, 15 Drawing Sheets
(10 of 15 Drawing Sheet(s) Filed in Color)

Related U.S. Application Data continuation of application No. 14/190,113, filed on Feb. 26, 2014, now Pat. No. 10,368,893, which is a division of application No. 13/049,013, filed on Mar. 16, 2011, now Pat. No. 8,696,581.

(60) Provisional application No. 61/393,947, filed on Oct. 18, 2010.

(51) Int. Cl.
*A61M 37/00* (2006.01)
*A61N 7/02* (2006.01)
*A61B 17/00* (2006.01)
*A61B 90/00* (2016.01)
*A61N 7/00* (2006.01)

(52) U.S. Cl.
CPC ............... *A61N 7/02* (2013.01); *A61N 7/022* (2013.01); *A61B 2017/00106* (2013.01); *A61B 2017/22008* (2013.01); *A61B 2017/22051* (2013.01); *A61B 2017/22081* (2013.01); *A61B 2090/378* (2016.02); *A61N 2007/0078* (2013.01)

(58) Field of Classification Search
CPC ........... A61B 2017/22051; A61B 2017/22081; A61B 2090/378; A61M 37/0092; A61N 7/02; A61N 7/022; A61N 2007/0078
See application file for complete search history.

(56) References Cited

U.S. PATENT DOCUMENTS

| | | |
|---|---|---|
| 5,226,847 A | 7/1993 | Thomas, III et al. |
| 5,421,338 A | 6/1995 | Crowley et al. |
| 5,467,251 A | 11/1995 | Katchmar |
| 5,471,988 A | 12/1995 | Fujio et al. |
| 5,494,039 A * | 2/1996 | Onik .................. A61B 17/3403 600/562 |
| 5,524,630 A | 6/1996 | Crowley |
| 5,590,653 A | 1/1997 | Aida et al. |
| 5,620,417 A | 4/1997 | Jang et al. |
| 5,620,479 A | 4/1997 | Diederich |
| 5,657,760 A | 8/1997 | Ying et al. |
| 5,699,804 A | 12/1997 | Rattner |
| 5,707,367 A | 1/1998 | Nilsson |
| 5,735,280 A | 4/1998 | Sherman et al. |
| 5,762,066 A | 6/1998 | Law et al. |
| 5,772,642 A | 6/1998 | Ciamacco, Jr. et al. |
| 5,895,355 A | 4/1999 | Schaer |
| 5,895,356 A | 4/1999 | Andrus et al. |
| 5,971,949 A | 10/1999 | Levin et al. |
| 6,007,499 A | 12/1999 | Martin et al. |
| 6,042,556 A | 3/2000 | Beach et al. |
| 6,073,048 A | 6/2000 | Kieval et al. |
| 6,077,225 A | 6/2000 | Brock-Fisher |
| 6,117,101 A | 9/2000 | Diederich et al. |
| 6,119,041 A | 9/2000 | Pomeranz et al. |
| 6,120,442 A | 9/2000 | Hickey |
| 6,165,127 A | 12/2000 | Crowley |
| 6,210,393 B1 * | 4/2001 | Brisken .................. A61F 2/958 128/898 |
| 6,216,041 B1 | 4/2001 | Tierney et al. |
| 6,235,024 B1 | 5/2001 | Tu |
| 6,261,233 B1 | 7/2001 | Kantorovich |
| 6,296,619 B1 | 10/2001 | Brisken et al. |
| 6,379,320 B1 | 4/2002 | Lafon et al. |
| 6,428,477 B1 | 8/2002 | Mason |
| 6,451,013 B1 | 9/2002 | Bays et al. |
| 6,500,121 B1 | 12/2002 | Slayton et al. |
| 6,511,428 B1 | 1/2003 | Azuma et al. |
| 6,511,436 B1 | 1/2003 | Asmar |
| 6,514,249 B1 | 2/2003 | Maguire et al. |
| 6,524,271 B2 | 2/2003 | Brisken et al. |
| 6,527,759 B1 * | 3/2003 | Tachibana .......... A61K 41/0047 604/509 |
| 6,547,788 B1 | 4/2003 | Maguire et al. |
| 6,575,906 B1 * | 6/2003 | Schembri, Jr. ....... A61B 8/4281 600/437 |
| 6,599,288 B2 | 7/2003 | Maguire et al. |
| 6,607,502 B1 | 8/2003 | Maguire et al. |
| 6,623,687 B1 | 9/2003 | Gervasi et al. |
| 6,645,147 B1 | 11/2003 | Jackson et al. |
| 6,740,040 B1 | 5/2004 | Mandrusov et al. |
| 6,752,805 B2 | 6/2004 | Maguire et al. |
| 6,953,460 B2 | 10/2005 | Maguire et al. |
| 6,955,173 B2 | 10/2005 | Lesh |
| 6,978,174 B2 | 12/2005 | Gelfand et al. |
| 7,001,336 B2 | 2/2006 | Mandrusov et al. |
| 7,037,271 B2 | 5/2006 | Crowley |
| 7,084,004 B2 | 8/2006 | Vaiyapuri et al. |
| 7,156,816 B2 | 1/2007 | Schwartz et al. |
| 7,162,303 B2 | 1/2007 | Levin et al. |
| 7,166,098 B1 | 1/2007 | Steward et al. |
| 7,220,233 B2 | 5/2007 | Nita et al. |
| 7,220,258 B2 | 5/2007 | Myhr |
| 7,220,261 B2 | 5/2007 | Truckai et al. |
| 7,285,116 B2 | 10/2007 | De la Rama et al. |
| 7,326,201 B2 | 2/2008 | Fjield et al. |
| 7,341,583 B2 | 3/2008 | Shiono et al. |
| 7,344,529 B2 | 3/2008 | Torchia et al. |
| 7,347,859 B2 | 3/2008 | Garabedian et al. |
| 7,410,486 B2 | 8/2008 | Fuimaono et al. |
| 7,460,369 B1 | 12/2008 | Blish, II |
| 7,470,241 B2 | 12/2008 | Weng et al. |
| 7,479,106 B2 | 1/2009 | Banik et al. |
| 7,510,536 B2 | 3/2009 | Foley et al. |
| 7,538,425 B2 | 5/2009 | Myers et al. |
| RE40,815 E | 6/2009 | Kudaravalli et al. |
| 7,540,846 B2 | 6/2009 | Harhen et al. |
| 7,540,870 B2 | 6/2009 | Babaev |
| 7,563,260 B2 | 7/2009 | Whitmore et al. |
| 7,617,005 B2 | 11/2009 | Demarais et al. |
| 7,620,451 B2 | 11/2009 | Demarais et al. |
| 7,621,929 B2 | 11/2009 | Nita et al. |
| 7,647,115 B2 | 1/2010 | Levin et al. |
| 7,653,438 B2 | 1/2010 | Deem et al. |
| 7,655,005 B2 | 2/2010 | Bhola |
| 7,678,104 B2 | 3/2010 | Keidar |
| 7,704,212 B2 | 4/2010 | Wekell et al. |
| 7,713,210 B2 | 5/2010 | Byrd et al. |
| 7,717,948 B2 | 5/2010 | Demarais et al. |
| 7,727,228 B2 | 6/2010 | Abboud et al. |
| 7,736,317 B2 | 6/2010 | Stephens et al. |
| 7,756,583 B2 | 7/2010 | Demarais et al. |
| 7,762,954 B2 | 7/2010 | Nix et al. |
| 7,771,372 B2 | 8/2010 | Wilson |
| 7,819,826 B2 | 10/2010 | Diederich et al. |
| 7,819,868 B2 | 10/2010 | Cao et al. |
| 7,824,348 B2 | 11/2010 | Barthe et al. |
| 7,850,683 B2 | 12/2010 | Elkins et al. |
| 7,850,685 B2 | 12/2010 | Kunis et al. |
| 7,853,333 B2 | 12/2010 | Demarais |
| 7,854,733 B2 | 12/2010 | Govari |
| 7,883,506 B2 | 2/2011 | McIntyre et al. |
| 7,940,969 B2 | 5/2011 | Nair et al. |
| 8,216,216 B2 | 7/2012 | Warnking et al. |
| 8,221,402 B2 | 7/2012 | Francischelli et al. |
| 8,401,667 B2 | 3/2013 | Gustus et al. |
| 8,419,729 B2 | 4/2013 | Ibrahim et al. |
| 8,540,662 B2 | 9/2013 | Stehr et al. |
| 8,568,403 B2 | 10/2013 | Soltesz et al. |
| 8,585,695 B2 | 11/2013 | Shih |
| 8,715,209 B2 * | 5/2014 | Gertner .................. A61B 8/06 601/3 |
| 8,974,446 B2 | 3/2015 | Nguyen et al. |
| 10,368,893 B2 | 4/2019 | Sverdlik et al. |
| 11,318,331 B2 | 5/2022 | Shabtay et al. |
| 2001/0007940 A1 | 7/2001 | Tu et al. |
| 2001/0014780 A1 | 8/2001 | Martin et al. |
| 2001/0053885 A1 | 12/2001 | Gielen et al. |
| 2002/0002371 A1 | 1/2002 | Acker et al. |
| 2002/0016624 A1 | 2/2002 | Patterson et al. |

(56) References Cited

U.S. PATENT DOCUMENTS

| | | |
|---|---|---|
| 2002/0019627 A1 | 2/2002 | Maguire et al. |
| 2002/0022833 A1 | 2/2002 | Maguire et al. |
| 2002/0026127 A1 | 2/2002 | Balbierz et al. |
| 2002/0048310 A1 | 4/2002 | Heuser |
| 2002/0055754 A1 | 5/2002 | Ranucci et al. |
| 2002/0065512 A1 | 5/2002 | Fjield et al. |
| 2002/0077643 A1 | 6/2002 | Rabiner et al. |
| 2002/0169394 A1 | 11/2002 | Eppstein et al. |
| 2002/0188218 A1 | 12/2002 | Lipman |
| 2003/0013968 A1 | 1/2003 | Fjield et al. |
| 2003/0092667 A1 | 5/2003 | Tachibana et al. |
| 2003/0125726 A1 | 7/2003 | Maguire et al. |
| 2003/0135115 A1* | 7/2003 | Burdette ............... A61N 5/103 600/437 |
| 2003/0151417 A1 | 8/2003 | Koen |
| 2003/0153850 A1* | 8/2003 | Davis ................. A61B 6/5235 601/2 |
| 2003/0158545 A1 | 8/2003 | Hovda et al. |
| 2003/0163190 A1 | 8/2003 | LaFont et al. |
| 2003/0181901 A1 | 9/2003 | Maguire et al. |
| 2003/0195496 A1 | 10/2003 | Maguire et al. |
| 2003/0199747 A1* | 10/2003 | Michlitsch ........... A61B 5/6853 600/407 |
| 2003/0199768 A1* | 10/2003 | Cespedes ............ A61B 5/6853 600/473 |
| 2004/0006333 A1 | 1/2004 | Arnold et al. |
| 2004/0019687 A1* | 1/2004 | Ozawa ................. H04L 63/083 709/229 |
| 2004/0073660 A1* | 4/2004 | Toomey ............... H04L 63/108 709/224 |
| 2004/0082859 A1 | 4/2004 | Schaer |
| 2004/0102361 A1 | 5/2004 | Bodin |
| 2004/0102769 A1 | 5/2004 | Schwartz et al. |
| 2004/0143358 A1 | 7/2004 | Silverbrook |
| 2004/0162458 A1* | 8/2004 | Green .................. A61N 5/1007 600/7 |
| 2005/0015079 A1 | 1/2005 | Keider |
| 2005/0020967 A1 | 1/2005 | Ono |
| 2005/0096542 A1 | 5/2005 | Weng et al. |
| 2005/0096647 A1 | 5/2005 | Steinke et al. |
| 2005/0159676 A1* | 7/2005 | Taylor ................ A61B 10/0275 600/564 |
| 2005/0215946 A1 | 9/2005 | Hansmann et al. |
| 2005/0240170 A1 | 10/2005 | Zhang et al. |
| 2005/0288730 A1 | 12/2005 | Deem et al. |
| 2006/0009753 A1 | 1/2006 | Fjield et al. |
| 2006/0052774 A1 | 3/2006 | Garrison et al. |
| 2006/0058711 A1 | 3/2006 | Harhen et al. |
| 2006/0079816 A1 | 4/2006 | Barthe et al. |
| 2006/0084966 A1 | 4/2006 | Maguire et al. |
| 2006/0173387 A1 | 8/2006 | Hansmann et al. |
| 2006/0229594 A1 | 10/2006 | Francischelli et al. |
| 2006/0241442 A1 | 10/2006 | Barthe et al. |
| 2006/0241739 A1 | 10/2006 | Besselink et al. |
| 2006/0264809 A1 | 11/2006 | Hansmann et al. |
| 2006/0287604 A1 | 12/2006 | Hickey |
| 2007/0043291 A1* | 2/2007 | Fidel .................... A61B 8/4281 600/439 |
| 2007/0043297 A1 | 2/2007 | Miyazawa |
| 2007/0088346 A1 | 4/2007 | Mirizzi et al. |
| 2007/0142831 A1 | 6/2007 | Shadduck |
| 2007/0142879 A1 | 6/2007 | Greenberg et al. |
| 2007/0167824 A1 | 7/2007 | Lee et al. |
| 2007/0203479 A1 | 8/2007 | Auth et al. |
| 2007/0222339 A1 | 9/2007 | Lukacs et al. |
| 2007/0225619 A1 | 9/2007 | Rabiner et al. |
| 2007/0233057 A1 | 10/2007 | Konishi |
| 2007/0249997 A1 | 10/2007 | Goodson et al. |
| 2007/0282407 A1 | 12/2007 | Demarais et al. |
| 2008/0004481 A1* | 1/2008 | Bax .................... A61B 17/3403 600/7 |
| 2008/0039745 A1 | 2/2008 | Babaev |
| 2008/0077202 A1 | 3/2008 | Levinson |
| 2008/0086073 A1 | 4/2008 | McDaniel |
| 2008/0114354 A1 | 5/2008 | Whayne et al. |
| 2008/0125829 A1 | 5/2008 | Velasco et al. |
| 2008/0139971 A1 | 6/2008 | Lockhart |
| 2008/0146924 A1 | 6/2008 | Smith et al. |
| 2008/0171934 A1 | 7/2008 | Greenan et al. |
| 2008/0179736 A1 | 7/2008 | Hartwell et al. |
| 2008/0183110 A1 | 7/2008 | Davenport et al. |
| 2008/0195000 A1 | 8/2008 | Spooner et al. |
| 2008/0213331 A1 | 9/2008 | Gelfand et al. |
| 2008/0214966 A1 | 9/2008 | Slayton et al. |
| 2008/0215039 A1 | 9/2008 | Slatkine et al. |
| 2008/0228111 A1 | 9/2008 | Nita |
| 2008/0249518 A1 | 10/2008 | Warnking et al. |
| 2008/0281297 A1 | 11/2008 | Pesach et al. |
| 2008/0300571 A1 | 12/2008 | LePivert |
| 2008/0300655 A1 | 12/2008 | Cholette |
| 2008/0312643 A1 | 12/2008 | Kania et al. |
| 2009/0018446 A1 | 1/2009 | Medan et al. |
| 2009/0030339 A1* | 1/2009 | Cheng ................. A61B 8/0841 600/562 |
| 2009/0036914 A1 | 2/2009 | Houser |
| 2009/0093737 A1 | 4/2009 | Chomas et al. |
| 2009/0131930 A1 | 5/2009 | Gelbart et al. |
| 2009/0149782 A1 | 6/2009 | Cohen et al. |
| 2009/0163807 A1 | 6/2009 | Sliwa |
| 2009/0216246 A1 | 8/2009 | Nita et al. |
| 2009/0221939 A1 | 9/2009 | Demarais et al. |
| 2009/0221955 A1 | 9/2009 | Babaev |
| 2009/0254078 A1 | 10/2009 | Just et al. |
| 2009/0281478 A1 | 11/2009 | Duke |
| 2009/0299360 A1 | 12/2009 | Ormsby |
| 2010/0036293 A1 | 2/2010 | Isola et al. |
| 2010/0081933 A1 | 4/2010 | Sverdlik et al. |
| 2010/0091112 A1 | 4/2010 | Veeser et al. |
| 2010/0114082 A1 | 5/2010 | Sharma |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0152625 A1 | 6/2010 | Milo |
| 2010/0168624 A1 | 7/2010 | Sliwa |
| 2010/0168649 A1* | 7/2010 | Schwartz ................. A61B 8/06 604/509 |
| 2010/0168731 A1 | 7/2010 | Wu et al. |
| 2010/0185156 A1 | 7/2010 | Kanner et al. |
| 2010/0191112 A1 | 7/2010 | Demarais et al. |
| 2010/0198040 A1 | 8/2010 | Friedman et al. |
| 2010/0210946 A1 | 8/2010 | Harada et al. |
| 2010/0222851 A1 | 9/2010 | Deem et al. |
| 2010/0228162 A1 | 9/2010 | Sliwa et al. |
| 2010/0262014 A1 | 10/2010 | Huang |
| 2010/0331686 A1 | 12/2010 | Hossack et al. |
| 2010/0331950 A1 | 12/2010 | Strommer |
| 2011/0009779 A1 | 1/2011 | Romano et al. |
| 2011/0028962 A1 | 2/2011 | Werneth et al. |
| 2011/0034809 A1 | 2/2011 | Eberle et al. |
| 2011/0066217 A1 | 3/2011 | Diller et al. |
| 2011/0071380 A1* | 3/2011 | Goldenberg ......... A61B 8/0841 600/411 |
| 2011/0092781 A1 | 4/2011 | Gertner |
| 2011/0092880 A1 | 4/2011 | Gertner |
| 2011/0106132 A1* | 5/2011 | Barbut ............... A61B 17/1204 606/194 |
| 2011/0112400 A1* | 5/2011 | Emery ..................... A61N 7/00 601/3 |
| 2011/0178441 A1 | 7/2011 | Tyler |
| 2011/0201973 A1 | 8/2011 | Stephens et al. |
| 2011/0257563 A1 | 10/2011 | Thapliyal et al. |
| 2011/0264075 A1 | 10/2011 | Leung et al. |
| 2011/0264086 A1 | 10/2011 | Ingle |
| 2011/0270247 A1 | 11/2011 | Sherman |
| 2011/0282203 A1* | 11/2011 | Tsoref .................. A61B 8/5223 600/443 |
| 2011/0282249 A1 | 11/2011 | Tsoref et al. |
| 2011/0301662 A1 | 12/2011 | Bar-Yoseph et al. |
| 2011/0319759 A1* | 12/2011 | Liu .................... A61B 10/0241 600/439 |
| 2011/0319765 A1* | 12/2011 | Gertner ................... A61N 7/02 600/453 |

(56) References Cited

U.S. PATENT DOCUMENTS

| | | | |
|---|---|---|---|
| 2012/0010512 A1* | 1/2012 | O'Laughlin | A61B 8/4254 600/459 |
| 2012/0016273 A1 | 1/2012 | Diederich | |
| 2012/0053577 A1 | 3/2012 | Lee et al. | |
| 2012/0065494 A1* | 3/2012 | Gertner | A61B 8/06 601/2 |
| 2012/0083717 A1 | 4/2012 | Alleman et al. | |
| 2012/0095335 A1 | 4/2012 | Sverdlik et al. | |
| 2012/0095371 A1 | 4/2012 | Sverdlik et al. | |
| 2012/0095372 A1 | 4/2012 | Sverdlik et al. | |
| 2012/0123243 A1 | 5/2012 | Hastings | |
| 2012/0123270 A1 | 5/2012 | Klee et al. | |
| 2012/0157841 A1* | 6/2012 | Glaenzer | A61B 10/0241 600/439 |
| 2012/0203098 A1 | 8/2012 | Raju et al. | |
| 2012/0209116 A1* | 8/2012 | Hossack | A61M 25/00 604/23 |
| 2012/0215106 A1 | 8/2012 | Sverdlik et al. | |
| 2012/0232409 A1 | 9/2012 | Stahmann et al. | |
| 2012/0232436 A1 | 9/2012 | Warnking | |
| 2012/0245455 A1* | 9/2012 | Bauman | A61B 17/3403 600/424 |
| 2012/0265227 A1 | 10/2012 | Sverdlik et al. | |
| 2012/0268886 A1 | 10/2012 | Leontiev et al. | |
| 2012/0283605 A1 | 11/2012 | Lewis, Jr. | |
| 2012/0310233 A1 | 12/2012 | Dimmer et al. | |
| 2012/0316559 A1 | 12/2012 | Mayse et al. | |
| 2013/0072928 A1 | 3/2013 | Schaer | |
| 2013/0123670 A1 | 5/2013 | Smith | |
| 2013/0131668 A1 | 5/2013 | Schaer | |
| 2013/0142875 A1* | 6/2013 | Shemi | A61K 9/7007 424/484 |
| 2013/0197555 A1* | 8/2013 | Schaer | A61N 7/022 606/170 |
| 2013/0204068 A1 | 8/2013 | Gnanashanmugam et al. | |
| 2013/0204167 A1 | 8/2013 | Sverdlik et al. | |
| 2013/0204242 A1 | 8/2013 | Sverdlik et al. | |
| 2013/0207519 A1 | 8/2013 | Chaggares et al. | |
| 2013/0211292 A1 | 8/2013 | Sverdlik et al. | |
| 2013/0211396 A1 | 8/2013 | Sverdlik et al. | |
| 2013/0211437 A1 | 8/2013 | Sverdlik et al. | |
| 2013/0218054 A1 | 8/2013 | Sverdlik et al. | |
| 2013/0218068 A1 | 8/2013 | Sverdlik et al. | |
| 2013/0225595 A1 | 8/2013 | Gillies et al. | |
| 2013/0226040 A1 | 8/2013 | Michael et al. | |
| 2013/0267875 A1 | 10/2013 | Thapliyal et al. | |
| 2013/0274607 A1 | 10/2013 | Anand et al. | |
| 2013/0296836 A1 | 11/2013 | Barbut et al. | |
| 2013/0310680 A1* | 11/2013 | Werahera | A61B 5/0035 600/478 |
| 2013/0310822 A1 | 11/2013 | Mayse et al. | |
| 2014/0005706 A1 | 1/2014 | Gelfand et al. | |
| 2014/0012133 A1 | 1/2014 | Sverdlik et al. | |
| 2014/0024975 A1 | 1/2014 | Little et al. | |
| 2014/0039286 A1 | 2/2014 | Hoffer | |
| 2014/0039314 A1* | 2/2014 | Stoianovici | A61B 8/0841 600/439 |
| 2014/0039477 A1 | 2/2014 | Sverdlik et al. | |
| 2014/0058294 A1 | 2/2014 | Gross et al. | |
| 2014/0074076 A1* | 3/2014 | Gertner | A61B 6/12 606/169 |
| 2014/0088585 A1 | 3/2014 | Hill et al. | |
| 2014/0114215 A1 | 4/2014 | Melder et al. | |
| 2014/0163540 A1 | 6/2014 | Iyer et al. | |
| 2014/0163652 A1 | 6/2014 | Witzel et al. | |
| 2014/0180197 A1 | 6/2014 | Sverdlik et al. | |
| 2014/0180277 A1 | 6/2014 | Chen | |
| 2014/0194866 A1 | 7/2014 | Wang | |
| 2014/0255647 A1 | 9/2014 | Johnson et al. | |
| 2014/0257262 A1 | 9/2014 | Carpentier et al. | |
| 2014/0276135 A1* | 9/2014 | Agah | A61M 25/1011 604/528 |
| 2014/0359111 A1* | 12/2014 | Hilmo | G06F 9/485 709/224 |
| 2015/0057599 A1 | 2/2015 | Chen | |
| 2015/0073400 A1 | 3/2015 | Sverdlik et al. | |
| 2015/0112234 A1* | 4/2015 | McCaffrey | A61N 7/02 601/3 |
| 2015/0119715 A1* | 4/2015 | Baumann | A61B 8/5215 600/407 |
| 2015/0150459 A1* | 6/2015 | Werahera | A61B 8/0841 600/476 |
| 2015/0199660 A1 | 7/2015 | Sarge et al. | |
| 2015/0242486 A1* | 8/2015 | Chari | G06F 16/35 707/737 |
| 2015/0272668 A1 | 10/2015 | Chen | |
| 2015/0366544 A1* | 12/2015 | Yap | A61B 10/04 600/464 |
| 2016/0059044 A1* | 3/2016 | Gertner | A61B 90/37 601/2 |
| 2016/0059489 A1 | 3/2016 | Wang et al. | |
| 2016/0113699 A1 | 4/2016 | Sverdlik et al. | |
| 2016/0374710 A1* | 12/2016 | Sinelnikov | A61B 17/3207 600/439 |
| 2017/0027645 A1 | 2/2017 | Ben Oren et al. | |
| 2017/0050374 A1 | 2/2017 | Minardi et al. | |
| 2017/0120333 A1 | 5/2017 | DeMuth et al. | |
| 2017/0246482 A1 | 8/2017 | Hananel et al. | |
| 2017/0312021 A1 | 11/2017 | Pilcher et al. | |
| 2017/0354461 A1 | 12/2017 | Rothman et al. | |
| 2018/0353203 A1 | 1/2018 | Lupotti et al. | |
| 2018/0055988 A1 | 3/2018 | Brun | |
| 2018/0326227 A1 | 11/2018 | Sverdlik et al. | |
| 2019/0290350 A1 | 9/2019 | Sverdlik et al. | |
| 2019/0308003 A1 | 10/2019 | Sverdlik et al. | |
| 2019/0366130 A1 | 12/2019 | Sverdlik et al. | |
| 2020/0238107 A1 | 7/2020 | Shabtay et al. | |
| 2020/0368244 A1 | 11/2020 | Shabtay et al. | |
| 2021/0178194 A1 | 6/2021 | Sverdlik et al. | |
| 2022/0241617 A1 | 8/2022 | Shabtay et al. | |
| 2022/0287634 A1 | 9/2022 | Sverdlik et al. | |

FOREIGN PATENT DOCUMENTS

| | | |
|---|---|---|
| CN | 101610735 | 12/2009 |
| CN | 101820820 | 9/2010 |
| EP | 1384445 | 1/2004 |
| EP | 1424100 | 6/2004 |
| EP | 1799302 | 3/2006 |
| EP | 1769759 | 4/2007 |
| EP | 1802370 | 7/2007 |
| EP | 2092957 | 8/2009 |
| EP | 2218479 | 8/2010 |
| EP | 2455133 | 5/2012 |
| JP | 07-227394 | 8/1995 |
| JP | 09-122139 | 5/1997 |
| JP | 10-248854 | 9/1998 |
| JP | 2008-536562 | 9/2008 |
| JP | 2010-517695 | 5/2010 |
| JP | 2019-018526 | 2/2019 |
| JP | 6650925 | 2/2020 |
| WO | WO 91/10405 | 7/1991 |
| WO | WO 99/16366 | 4/1999 |
| WO | WO 00/67648 | 10/2000 |
| WO | WO 01/45550 | 6/2001 |
| WO | WO 02/096501 | 12/2002 |
| WO | WO 2004/054448 | 7/2004 |
| WO | WO 2006/022790 | 3/2006 |
| WO | WO 2006/041847 | 4/2006 |
| WO | WO 2006/041881 | 4/2006 |
| WO | WO 2006/042163 | 4/2006 |
| WO | WO 2007/001981 | 1/2007 |
| WO | WO 2007/078997 | 7/2007 |
| WO | WO 2007/115307 | 10/2007 |
| WO | WO 2007/127176 | 11/2007 |
| WO | WO 2008/003058 | 1/2008 |
| WO | WO 2008/098101 | 8/2008 |
| WO | WO 2008/102363 | 8/2008 |
| WO | WO 2010/009473 | 1/2010 |
| WO | WO 2010/118307 | 10/2010 |
| WO | WO 2011/053757 | 5/2011 |
| WO | WO 2011/060200 | 5/2011 |

(56) References Cited

FOREIGN PATENT DOCUMENTS

| WO | WO 2011/075328 | 6/2011 |
|---|---|---|
| WO | WO 2012/052920 | 4/2012 |
| WO | WO 2012/052921 | 4/2012 |
| WO | WO 2012/052922 | 4/2012 |
| WO | WO 2012/052924 | 4/2012 |
| WO | WO 2012/052925 | 4/2012 |
| WO | WO 2012/052926 | 4/2012 |
| WO | WO 2012/052927 | 4/2012 |
| WO | WO 2012/082927 | 4/2012 |
| WO | WO 2012/061713 | 5/2012 |
| WO | WO 2013/030743 | 3/2013 |
| WO | WO 2013/111136 | 8/2013 |
| WO | WO 2013/134479 | 9/2013 |
| WO | WO 2013/157009 | 10/2013 |
| WO | WO 2013/157011 | 10/2013 |
| WO | WO 2013/162694 | 10/2013 |
| WO | WO 2014/141052 | 9/2014 |
| WO | WO 2014/188430 | 11/2014 |
| WO | WO 2016/084081 | 6/2016 |
| WO | WO 2016/084081 A8 | 6/2017 |
| WO | WO 2018/173052 | 9/2018 |
| WO | WO 2018/173053 | 9/2018 |

OTHER PUBLICATIONS

Advisory Action Dated Jun. 16, 2020 from the US Patent and Trademark Office Re. U.S. Appl. No. 13/449,539. (5 pages).
Applicant-Initiated Interview Summary Dated Apr. 2, 2019 From the US Patent and Trademark Office Re. U.S. Appl. No. 13/905,224. (3 pages).
Applicant-Initiated Interview Summary Dated Jan. 4, 2016 From the US Patent and Trademark Office Re. U.S. Appl. No. 13/449,539.
Applicant-Initiated Interview Summary Dated Jul. 14, 2016 From the US Patent and Trademark Office Re. U.S. Appl. No. 13/449,539.
Applicant-Initiated Interview Summary Dated Nov. 14, 2018 From the US Patent and Trademark Office Re. U.S. Appl. No. 13/449,539. (3 pages).
Applicant-Initiated Interview Summary Dated Jan. 21, 2015 From the US Patent and Trademark Office Re. U.S. Appl. No. 13/449,539.
Applicant-Initiated Interview Summary Dated Feb. 22, 2016 From the US Patent and Trademark Office Re. U.S. Appl. No. 13/880,066.
Applicant-Initiated Interview Summary Dated Jan. 24, 2014 From the US Patent and Trademark Office Re. U.S. Appl. No. 13/449,539.
Applicant-Initiated Interview Summary Dated Apr. 25, 2018 From the US Patent and Trademark Office Re. U.S. Appl. No. 14/394,276. (3 pages).
Applicant-Initiated Interview Summary Dated Sep. 28, 2016 From the US Patent and Trademark Office Re. U.S. Appl. No. 13/905,224.
Communication Pursuant to Article 94(3) EPC Dated Mar. 1, 2023 From the European Patent Office Re. Application No. 18771348.2 (6 Pages).
Communication Pursuant to Article 94(3) EPC Dated Dec. 2, 2020 From the European Patent Office Re. Application No. 15862313.2. (9 Pages).
Communication Pursuant to Article 94(3) EPC Dated Nov. 4, 2014 From the European Patent Office Re. Application No. 11833950.6.
Communication Pursuant to Article 94(3) EPC Dated Feb. 8, 2016 From the European Patent Office Re. Application No. 11833950.6.
Communication Pursuant to Article 94(3) EPC Dated Apr. 10, 2015 From the European Patent Office Re. Application No. 11782222.1.
Communication Pursuant to Article 94(3) EPC Dated Jun. 10, 2014 From the European Patent Office Re. Application No. 11822476.3.
Communication Pursuant to Article 94(3) EPC Dated Jun. 10, 2014 From the European Patent Office Re. Application No. 11784782.2.
Communication Pursuant to Article 94(3) EPC Dated Apr. 14, 2014 From the European Patent Office Re. Application No. 11782221.3.
Communication Pursuant to Article 94(3) EPC Dated Jul. 20, 2016 From the European Patent Office Re. Application No. 11782221.3.
Communication Pursuant to Article 94(3) EPC Dated Sep. 26, 2014 From the European Patent Office Re. Application No. 11782222.1.
Communication Pursuant to Article 94(3) EPC Dated Jul. 27, 2016 From the European Patent Office Re. Application No. 11782222.1.
Communication Pursuant to Article 94(3) EPC Dated Oct. 30, 2014 From the European Patent Office Re. Application No. 11782221.3.
Communication Pursuant to Rule 164(1) EPC: Supplementary Partial European Search Report and the European Provisional Opinion Dated May 18, 2018 From the European Patent Office Re. Application No. 15862313.2. (15 Pages).
Decision of Rejection Dated Sep. 2, 2022 From the China National Intellectual Property Administration Re. Application No. 20188003196.2 and its Summary in English. (4 Pages).
Decision of Rejection Dated Apr. 28, 2016 From the Japanese Patent Office Re. Application No. 2013-534435 and Its Machine Translation in English.
Final Official Action Dated Jun. 3, 2021 From the US Patent and Trademark Office Re. U.S. Appl. No. 13/905,224. (17 Pages).
Final Official Action Dated Jul. 12, 2022 from US Patent and Trademark Office Re. U.S. Appl. No. 16/494,322. (28 pages).
Final Official Action Dated Sep. 15, 2022 from US Patent and Trademark Office Re. U.S. Appl. No. 16/451,087. (13 pages).
International Preliminary Report on Patentability Dated May 2, 2013 From the International Bureau of WIPO Re. Application No. PCT/IB2011/054634.
International Preliminary Report on Patentability Dated May 2, 2013 From the International Bureau of WIPO Re. Application No. PCT/IB2011/054635.
International Preliminary Report on Patentability Dated May 2, 2013 From the International Bureau of WIPO Re. Application No. PCT/IB2011/054636.
International Preliminary Report on Patentability Dated May 2, 2013 From the International Bureau of WIPO Re. Application No. PCT/IB2011/054638.
International Preliminary Report on Patentability Dated May 2, 2013 From the International Bureau of WIPO Re. Application No. PCT/IB2011/054639.
International Preliminary Report on Patentability Dated May 2, 2013 From the International Bureau of WIPO Re. Application No. PCT/IB2011/054640.
International Preliminary Report on Patentability Dated May 2, 2013 From the International Bureau of WIPO Re. Application No. PCT/IB2011/054641.
International Preliminary Report on Patentability Dated Dec. 3, 2015 From the International Bureau of WIPO Re. Application No. PCT/IL2014/050457.
International Preliminary Report on Patentability Dated Oct. 3, 2019 From the International Bureau of WIPO Re. Application No. PCT/IL2018/050321. (11 Pages).
International Preliminary Report on Patentability Dated Oct. 3, 2019 From the International Bureau of WIPO Re. Application No. PCT/IL2018/050322. (16 Pages).
International Preliminary Report on Patentability Dated Aug. 7, 2014 From the International Bureau of WIPO Re. Application No. PCT/IL2013/050068.
International Preliminary Report on Patentability Dated Jun. 8, 2017 From the International Bureau of WIPO Re. Application No. PCT/IL2015/051145. (16 Pages).
International Preliminary Report on Patentability Dated Oct. 30, 2014 From the International Bureau of WIPO Re. Application No. PCT/IL2013/050339.
International Preliminary Report on Patentability Dated Oct. 30, 2014 From the International Bureau of WIPO Re. Application No. PCT/IL2013/050341.
International Search Report and the Written Opinion Dated May 2, 2016 From the International Searching Authority Re. Application No. PCT/IL2015/051145.
International Search Report and the Written Opinion Dated Feb. 7, 2012 From the International Searching Authority Re. Application No. PCT/IB2011/054641.
International Search Report and the Written Opinion Dated Oct. 11, 2013 From the International Searching Authority Re. Application No. PCT/IL2013/050341.

(56) References Cited

OTHER PUBLICATIONS

International Search Report and the Written Opinion Dated Sep. 19, 2013 From the International Searching Authority Re. Application No. PCT/IL2013/050068.
International Search Report and the Written Opinion Dated Nov. 20, 2014 From the International Searching Authority Re. Application No. PCT/IL2014/050457.
International Search Report and the Written Opinion Dated Jun. 22, 2012 From the International Searching Authority Re. Application No. PCT/IB2011/054640.
International Search Report and the Written Opinion Dated Jan. 23, 2012 From the International Searching Authority Re. Application No. PCT/IB2011/054635.
International Search Report and the Written Opinion Dated Jan. 25, 2012 From the International Searching Authority Re. Application No. PCT/IB2011/054636.
International Search Report and the Written Opinion Dated Jan. 27, 2012 From the International Searching Authority Re. Application No. PCT/IB2011/054634.
International Search Report and the Written Opinion Dated Jan. 27, 2012 From the International Searching Authority Re. Application No. PCT/IB2011/054638.
International Search Report and the Written Opinion Dated Aug. 28, 2018 From the International Searching Authority Re. Application No. PCT/IL2018/050322. (40 Pages).
International Search Report and the Written Opinion Dated Aug. 29, 2018 From the International Searching Authority Re. Application No. PCT/IL2018/050321. (16 Pages).
International Search Report and the Written Opinion Dated Jan. 31, 2012 From the International Searching Authority Re. Application No. PCT/IB2011/054639.
Interview Summary Dated Jun. 5, 2023 from the US Patent and Trademark Office Re. U.S. Appl. No. 16/540,191. (3 pages).
Invitation Pursuant to Rule 137(4) EPC Dated Apr. 4, 2014 From the European Patent Office Re. Application No. 11785792.0.
Invitation Pursuant to Rule 137(4) EPC Dated Apr. 8, 2014 From the European Patent Office Re. Application No. 11782222.1.
Invitation Pursuant to Rule 137(4) EPC Dated Apr. 10, 2014 From the European Patent Office Re. Application No. 11782476.3.
Invitation Pursuant to Rule 137(4) EPC Dated Mar. 21, 2016 From the European Patent Office Re. Application No. 11782222.1.
Invitation to Pay Additional Fees Dated Sep. 3, 2013 From the International Searching Authority Re. Application No. PCT/IL2013/050339.
Invitation to Pay Additional Fees Dated Mar. 4, 2016 From the International Searching Authority Re. Application No. PCT/IL2015/051145.
Invitation to Pay Additional Fees Dated Sep. 4, 2014 From the International Searching Authority Re. Application No. PCT/IL2014/050457.
Invitation to Pay Additional Fees Dated Aug. 5, 2013 From the International Searching Authority Re. Application No. PCT/IL2013/050341.
Invitation to Pay Additional Fees Dated Apr. 17, 2012 From the International Searching Authority Re. Application No. PCT/IB2011/054640.
Invitation to Pay Additional Fees Dated Jun. 21, 2018 From the International Searching Authority Re. Application No. PCT/IL2018/050322. (3 Pages).
Invitation to Pay Additional Fees Dated Jul. 24, 2013 From the International Searching Authority Re. Application No. PCT/IL2013/050068.
Invitation to Pay Additional Fees Dated Jun. 25, 2018 From the International Searching Authority Re. Application No. PCT/IL2018/050321. (2 Pages).
Notice of Allowance Dated Apr. 3, 2023 from US Patent and Trademark Office Re. U.S. Appl. No. 16/451,087. (9 pages).
Notice of Allowance Dated Mar. 6, 2019 From the US Patent and Trademark Office Re. U.S. Appl. No. 14/394,276. (11 Pages).
Notice of Allowance Dated Oct. 6, 2014 From the US Patent and Trademark Office Re. U.S. Appl. No. 13/880,061.
Notice of Allowance Dated Nov. 7, 2013 From the US Patent and Trademark Office Re. U.S. Appl. No. 13/049,013.
Notice of Allowance Dated Dec. 8, 2015 From the US Patent and Trademark Office Re. U.S. Appl. No. 14/049,238.
Notice of Allowance Dated Jan. 8, 2015 From the US Patent and Trademark Office Re. U.S. Appl. No. 13/880,061.
Notice of Allowance Dated Feb. 10, 2022 from US Patent and Trademark Office Re. U.S. Appl. No. 13/905,224. (8 pages).
Notice of Allowance Dated Aug. 11, 2020 from the US Patent and Trademark Office Re. U.S. Appl. No. 13/449,539. (11 pages).
Notice of Allowance Dated Sep. 14, 2016 From the US Patent and Trademark Office Re. U.S. Appl. No. 13/879,400.
Notice of Allowance Dated Jul. 18, 2016 From the US Patent and Trademark Office Re. U.S. Appl. No. 13/879,400.
Notice of Allowance Dated Jun. 21, 2013 From the US Patent and Trademark Office Re. U.S. Appl. No. 13/049,151.
Notice of Allowance Dated Sep. 23, 2020 from the US Patent and Trademark Office Re. U.S. Appl. No. 14/889,890. (8 pages).
Notice of Allowance Dated Mar. 26, 2019 From the US Patent and Trademark Office Re. U.S. Appl. No. 14/190,113. (8 pages).
Notice of Allowance Dated Dec. 29, 2021 from US Patent and Trademark Office Re. U.S. Appl. No. 16/494,321. (51 pages).
Notice of Non-Compliant Amendment Dated Sep. 23, 2015 From the US Patent and Trademark Office Re. U.S. Appl. No. 13/880,124.
Notice of Reason for Rejection Dated Aug. 25, 2015 From the Japanese Patent Office Re. Application No. 2013-534435.
Notification of Office Action and Search Report Dated Apr. 1, 2021 From the State Intellectual Property Office of the People's Republic of China Re. Application No. 201880031396.2 and Its Translation of Office Action Into English. (9 Pages).
Notification of Office Action and Search Report Dated Dec. 1, 2014 From The State Intellectual Property Office of the People's Republic of China Re. Application No. 201180060862.8.
Notification of Office Action and Search Report Dated Mar. 14, 2022 From the State Intellectual Property Office of the People's Republic of China Re. Application No. 20188003196.2 and Its Translation of Office Action Into English. (15 Pages).
Office Action Dated Jul. 30, 2014 From the State Intellectual Property Office of the People's Republic of China Re. Application No. 201180060741.3 and Its Summary in English.
Official Action Dated Aug. 2, 2021 from the US Patent and Trademark Office Re. U.S. Appl. No. 16/494,321. (10 pages).
Official Action Dated Jul. 2, 2015 From the US Patent and Trademark Office Re. U.S. Appl. No. 13/879,400.
Official Action Dated Apr. 3, 2023 from the US Patent and Trademark Office Re. U.S. Appl. No. 17/187,813. (55 pages).
Official Action Dated Dec. 3, 2014 From the US Patent and Trademark Office Re. U.S. Appl. No. 13/462,956.
Official Action Dated Jun. 3, 2016 From the US Patent and Trademark Office Re. U.S. Appl. No. 13/880,066.
Official Action Dated Jun. 3, 2019 From the US Patent and Trademark Office Re. U.S. Appl. No. 13/449,539. (13 Pages).
Official Action Dated Mar. 3, 2023 from the US Patent and Trademark Office Re. U.S. Appl. No. 16/540,191. (56 pages).
Official Action Dated Nov. 3, 2017 From the US Patent and Trademark Office Re. U.S. Appl. No. 14/394,276. (11 pages).
Official Action Dated Nov. 4, 2014 From the US Patent and Trademark Office Re. U.S. Appl. No. 13/879,400.
Official Action Dated Aug. 5, 2015 From the US Patent and Trademark Office Re. U.S. Appl. No. 13/905,224.
Official Action Dated Jan. 5, 2016 From the US Patent and Trademark Office Re. U.S. Appl. No. 13/880,124.
Official Action Dated Jun. 5, 2015 From the US Patent and Trademark Office Re. U.S. Appl. No. 14/049,238.
Official Action Dated Nov. 5, 2014 From the US Patent and Trademark Office Re. U.S. Appl. No. 13/049,022.
Official Action Dated Feb. 6, 2015 From the US Patent and Trademark Office Re. U.S. Appl. No. 14/190,113.
Official Action Dated Jan. 6, 2017 From the US Patent and Trademark Office Re. U.S. Appl. No. 14/190,113. (11 pages).

(56) References Cited

OTHER PUBLICATIONS

Official Action Dated Oct. 7, 2014 From the US Patent and Trademark Office Re. U.S. Appl. No. 13/880,109.
Official Action Dated May 8, 2013 From the US Patent and Trademark Office Re. U.S. Appl. No. 13/462,956.
Official Action Dated Aug. 10, 2018 From the US Patent and Trademark Office Re. U.S. Appl. No. 14/190,113. (11 Pages).
Official Action Dated Jun. 10, 2016 From the US Patent and Trademark Office Re. U.S. Appl. No. 14/190,113.
Official Action Dated Mar. 10, 2016 From the US Patent and Trademark Office Re. U.S. Appl. No. 13/449,539.
Official Action Dated Sep. 10, 2014 From the US Patent and Trademark Office Re. U.S. Appl. No. 14/049,238.
Official Action Dated Mar. 11, 2021 from the US Patent and Trademark Office Re. U.S. Appl. No. 16/494,321. (7 pages).
Official Action Dated Oct. 11, 2018 From the US Patent and Trademark Office Re. U.S. Appl. No. 14/394,276. (200 Pages).
Official Action Dated Sep. 11, 2015 From the US Patent and Trademark Office Re. U.S. Appl. No. 13/880,066.
Official Action Dated Apr. 13, 2020 from the US Patent and Trademark Office Re. U.S. Appl. No. 14/889,890. (23 pages).
Official Action Dated Aug. 13, 2020 from the US Patent and Trademark Office Re. U.S. Appl. No. 13/905,224. (24 pages).
Official Action Dated Apr. 14, 2014 From the US Patent and Trademark Office Re. U.S. Appl. No. 13/879,400.
Official Action Dated Aug. 14, 2015 From the US Patent and Trademark Office Re. U.S. Appl. No. 13/449,539.
Official Action Dated May 16, 2019 From the US Patent and Trademark Office Re. U.S. Appl. No. 15/529,137. (11 pages).
Official Action Dated Oct. 16, 2019 From the US Patent and Trademark Office Re. U.S. Appl. No. 13/449,539.(8 Pages).
Official Action Dated Jul. 17, 2013 From the US Patent and Trademark Office Re. U.S. Appl. No. 13/049,013.
Official Action Dated Nov. 17, 2017 From the US Patent and Trademark Office Re. U.S. Appl. No. 13/905,224. (19 pages).
Official Action Dated Dec. 19, 2013 From the US Patent and Trademark Office Re. U.S. Appl. No. 13/049,022.
Official Action Dated Mar. 20, 2014 From the US Patent and Trademark Office Re. U.S. Appl. No. 13/449,539.
Official Action Dated Oct. 20, 2017 From the US Patent and Trademark Office Re. U.S. Appl. No. 14/190,113. (7 pages).
Official Action Dated Apr. 21, 2017 From the US Patent and Trademark Office Re. U.S. Appl. No. 14/394,276. (13 pages).
Official Action Dated Feb. 21, 2019 From the US Patent and Trademark Office Re. U.S. Appl. No. 14/889,890. (19 pages).
Official Action Dated Jan. 21, 2022 From the US Patent and Trademark Office Re. U.S. Appl. No. 16/451,087. (150 Pages).
Official Action Dated Jun. 21, 2018 From the US Patent and Trademark Office Re. U.S. Appl. No. 13/449,539. (8 pages).
Official Action Dated Apr. 23, 2014 From the US Patent and Trademark Office Re. U.S. Appl. No. 13/880,061.
Official Action Dated Jun. 23, 2023 From the US Patent and Trademark Office Re. U.S. Appl. No. 17/752,879. (53 Pages).
Official Action Dated Sep. 23, 2022 from US Patent and Trademark Office Re. U.S. Appl. No. 16/540,191. (14 pages).
Official Action Dated May 24, 2023 from the US Patent and Trademark Office Re. U.S. Appl. No. 16/494,322. (113 pages).
Official Action Dated Oct. 24, 2012 From the US Patent and Trademark Office Re. U.S. Appl. No. 13/049,013.
Official Action Dated Oct. 24, 2019 From the US Patent and Trademark Office Re. U.S. Appl. No. 14/889,890. (54 pages).
Official Action Dated Sep. 25, 2013 From the US Patent and Trademark Office Re. U.S. Appl. No. 13/462,956.
Official Action Dated Sep. 25, 2015 From the US Patent and Trademark Office Re. U.S. Appl. No. 14/190,113.
Official Action Dated Jul. 26, 2016 From the US Patent and Trademark Office Re. U.S. Appl. No. 13/880,124.
Official Action Dated Jun. 26, 2023 from the US Patent and Trademark Office Re. U.S. Appl. No. 16/439,816. (59 pages).
Official Action Dated Dec. 27, 2016 From the US Patent and Trademark Office Re. U.S. Appl. No. 13/449,539. (13 pages).
Official Action Dated Apr. 29, 2016 From the US Patent and Trademark Office Re. U.S. Appl. No. 13/905,224.
Official Action Dated Aug. 29, 2013 From the US Patent and Trademark Office Re. U.S. Appl. No. 13/449,539.
Official Action Dated Jan. 29, 2013 From the US Patent and Trademark Office Re. U.S. Appl. No. 13/049,151.
Official Action Dated Aug. 31, 2021 from the US Patent and Trademark Office Re. U.S. Appl. No. 16/494,322. (27 pages).
Official Action Dated Oct. 31, 2018 From the US Patent and Trademark Office Re. U.S. Appl. No. 13/905,224. (23 pages).
Restriction Official Action Dated Aug. 1, 2023 from the US Patent and Trademark Office Re. U.S. Appl. No. 17/719,412. (8 pages).
Restriction Official Action Dated Jan. 4, 2019 From the US Patent and Trademark Office Re. U.S. Appl. No. 15/529,137. (8 pages).
Restriction Official Action Dated Oct. 5, 2012 From the US Patent and Trademark Office Re. U.S. Appl. No. 13/049,151.
Restriction Official Action Dated Jul. 7, 2014 From the US Patent and Trademark Office Re. U.S. Appl. No. 14/049,238.
Restriction Official Action Dated Apr. 14, 2015 From the US Patent and Trademark Office Re. U.S. Appl. No. 13/880,124.
Restriction Official Action Dated Dec. 14, 2022 from the US Patent and Trademark Office Re. U.S. Appl. No. 17/187,813. (8 pages).
Restriction Official Action Dated Nov. 17, 2014 From the US Patent and Trademark Office Re. U.S. Appl. No. 13/880,066.
Restriction Official Action Dated May 24, 2018 From the US Patent and Trademark Office Re. U.S. Appl. No. 14/889,890. (8 pages).
Restriction Official Action Dated Feb. 27, 2015 From the US Patent and Trademark Office Re. U.S. Appl. No. 13/905,224.
Restriction Official Action Dated Mar. 27, 2015 From the US Patent and Trademark Office Re. U.S. Appl. No. 13/880,095.
Restriction Official Action Dated Oct. 27, 2016 From the US Patent and Trademark Office Re. U.S. Appl. No. 14/394,276.
Restriction Official Action Dated Jun. 28, 2013 From the US Patent and Trademark Office Re. U.S. Appl. No. 13/449,539.
Restriction Official Action Dated Aug. 30, 2012 From the US Patent and Trademark Office Re. U.S. Appl. No. 13/049,013.
Restriction Official Action Dated Oct. 30, 2014 From the US Patent and Trademark Office Re. U.S. Appl. No. 13/880,083.
Search Report Dated Jul. 17, 2014 From the State Intellectual Property Office of the People's Republic of China Re. Application No. 201180060741.3 and Its Machine Translation in English.
Summons to Attend Oral Proceedings Pursuant to Rule 115(1) EPC Dated Mar. 11, 2022 From the European Patent Office Re. Application No. 15862313.2. (12 Pages).
Supplemental Notice of Allowance Dated Mar. 31, 2022 from US Patent and Trademark Office Re. U.S. Appl. No. 16/494,321. (4 pages).
Supplementary European Search Report and the European Search Opinion Dated Dec. 4, 2020 From the European Patent Office Re. Application No. 18771348.2. (9 Pages).
Supplementary European Search Report and the European Search Opinion Dated Sep. 5, 2018 From the European Patent Office Re. Application No. 15862313.2. (13 Pages).
Supplementary European Search Report and the European Search Opinion Dated Dec. 22, 2016 From the European Patent Office Re. Application No. 14801877.3. (9 Pages).
Supplementary European Search Report Dated Mar. 12, 2014 From the European Patent Office Re. Application No. 11833950.6.
Translation Dated Mar. 12, 2015 of Notification of Office Action and Search Report Dated Dec. 1, 2014 From the State Intellectual Property Office of the People's Republic of China Re. Application No. 201180060862.8.
Translation Dated Nov. 18, 2015 of Notice of Reason for Rejection Dated Aug. 25, 2015 From the Japanese Patent Office Re. Application No. 2013-534435.
Ahmed et al. "Renal Sympathetic Denervation Using an Irrigated Radiofrequency Ablation Catheter for the Management of Drug-Resistant Hypertension", Journal of the American College of Cardiology: Cardiovascular Interventions, JACC, 5(7): 758-765, 2012.

(56) References Cited

OTHER PUBLICATIONS

Ali et al. "Signal Processing Overview of Ultrasound Systems for Medical Imaging", Texas Instruments White Paper, SPRAB12: 1-27, Nov. 2008.
Anonymus "Indication for and Results of Sympathectomy in Patients With Peripheral Vascular Disease", Lumbar Sympathectomy, Poster, 34 P., 2009.
Aoyama et al. "Comparison of Cryothermia and Radiofrequency Current in Safety and Efficacy of Catheter Ablation Within the Canine Coronary Sinus Close to the Left Circumflex Coronary Artery", Journal of Cardiovascular Electrophysiology, 16: 1218-1226, Nov. 2005.
Atherton et al. "Micro-Anatomy of the Renal Sympathetic Nervous System: A Human Postmortem Histologic Study", Clinical Anatomy, p. 1-6, Oct. 4, 2011.
Bailey et al. "Cavitation Detection During Shock-Wave Lithotripsy", Ultrasound in Medicine and Biology, XP027605630, 31(9): 1245-1256, Sep. 1, 2005. Abstract, Fig.1, p. 1246, p. 1247, r-h col. p. 1249, r-h Col.
Baker et al. "Operative Lumbar Sympathectomy for Severe Lower Limb Ischaemia: Still A Valuable Treatment Option", Annals of the Royal College of Surgeons of England, 76(1): 50-53, Jan. 1994.
Bambi et al. "Real-Time Digital Processing of Doppler Ultrasound Signals", IEEE International Conference on Acoustics, Speech, and Signal Processing, Proceedings, (ICASSP '05), (5): v/977-v/980, Mar. 23-23, 2005.
Bandyopadhyay et al. "Outcomes of Beta-Blocker Use in Pulmonary Arterial Hypertension: A Propensity-Matched Analysis", European Respiratory Journal, 46(3): 750-760, Published Online May 28, 2015.
Bharat et al. "Monitoring Stiffness Changes in Lesions After Radiofrequency Ablation at Different Temperatures and Durations of Ablation", Ultrasound in Medicine & Biology, 31(3): 415-422, 2005.
Bhatt et al. "A Controlled Trial of Renal Denervation for Resistant Hypertension", The New England Journal of Medicine, 270(15): 1393-1401, Published Online Mar. 29, 2014.
Blankestijn et al. "Renal Denervation: Potential Impact on Hypertension in Kidney Disease?", Nephrology, Dialysis, Transplantation, 26(9): 2732-2734, Apr. 19, 2011.
Brandt et al. "Effects of Renal Sympathetic Denervation on Arterial Stiffness and Central Hemodynamics in Patients With Resistant Hypertension", Journal of the American College of Cardiology, 60(19): 1956-1965, 2012.
Brandt et al. "Renal Sympathetic Denervation Reduces Left Ventricular Hypertrophy and Improves Cardiac Function in Patients With Resistant Hypertension", Journal of the American College of Cardiology, 59(10): 901-909, 2012.
Brasselet et al. "Effect of Local Heating on Restenosis and In-Stent Neointimal Hyperplasia in the Atherosclerotic Rabbit Model: A Dose-Ranging Study", European Heart Journal, 29: 402-412, 2008.
Brinton et al. "Externally Focused Ultrasound for Sympathetic Renal Denervation", WAVE I First-in-Man Study, Kona Medical Inc., PowerPoint Presentation, TCT 2012, 15 P., 2012.
Campese et al. "Renal Afferent Denervation Prevents the Progression of Renal Disease in the Renal Ablation Model of Chronic Renal Failure in the Rat", American Journal of Kidney Diseases, 26(5): 861-865, Nov. 1995. Abstract.
Campese et al. "Sympathetic Renal Innervation and Resistant Hypertension", International Journal of Hypertension, 2011(Art.ID 814354): 1-6, 2011.
Cardiosonic "Cardiosonic New Applications", Cardiosonic, p. 1-20, Mar. 2014.
Cardiosonic "Histological Map of Swine Pulmonary Arteries", Cardiosonic, Animal #223, Mar. 26, 2014.
Cardiosonic "Histological Map of Swine Pulmonary Arteries", Cardiosonic, Animal #234, Mar. 18, 2014.
Cardiosonic "Histological Map of Swine Pulmonary Arteries", Cardiosonic, Animal #234, Mar. 26, 2014.
Cardiosonic "Histopathology Report", Cardiosonic, 2 P., Dec. 26, 2013.
Cardiosonic "PA/Trachea—Feedback Provisional", Cardiosonic, 5 P, Jun. 9, 2014.
Cardiosonic "PAH Preliminary Development Meeting Minutes", Cardiosonic, 2 P., Mar. 23, 2014.
Cheever "An Overview of Pulmonary Arterial Hypertension: Risks, Pathogenesis, Clinical Manifestations, and Management", The Journal of Cardiovascular Nursing 20(2): 108-116, Mar. 2005. Abstract.
Chen et al. "Artery Denervation to Treat Pulmonary Arterial Hypertension. The Single-Center, Prospective, First-in-Man PADN-1 Study (First-in-Man Pulmonary Artery Denervation for Treatment of Pulmonary Artery Hypertension)", Journal of the American College of Cardiology, JACC, 62(12): 1092-1100, Sep. 17, 2013.
Chen et al. "Hemodynamic, Functional, and Clinical Responses to Pulmonary Artery Denervation in Patients With Pulmonary Arterial Hypertension of Different Causes: Phase II Results From the Pulmonary Artery Denervation-1 Study", Circulation: Cardiovascular Interventions, 8(11): e002837-1-e002837-10, Nov. 9, 2015.
Chen et al. "Percutaneous Pulmonary Artery Denervation Completely Abolishes Experimental Pulmonary Arterial Hypertension In Vivo", EuroIntervention, 9(2): 269-276, Jun. 22, 2013.
Ciarka et al. "Prognostic Significance of Sympathetic Nervous System Activation in Pulmonary Arterial Hypertension", American Journal of Respiratory and Critical Care Medicine, 181(11): 1269-1275, Published Online Mar. 1, 2010.
CIBIS-II Investigators and Committees "The Cardiac Insufficiency Bisoprolol Study Ii (CIBIS-II): A Randomised Trial", The Lancet, 353(9146): 9-13, Jan. 2, 1999.
Cohn et al. "A Comparison of Enalapril With Hydralazine-Isosorbide Dinitrate in the Treatment of Chronic Congestive Heart Failure", The New England Journal of Medicine, 325(5): 303-310, Aug. 1, 1991.
CONSENSUS Trial Study Group "Effects of Enalapril on Mortality in severe Congestive Heart Failure. Results of the Cooperative North Scandinavian Enalapril Survival Study (CONSENSUS)", The New England Journal of Medicine, 316(23): 1429-1435, Jun. 4, 1987.
Copty et al. "Localized Heating of Biological Media Using A 1-W Microwave Near-Field Probe", IEEE Transactions on Microwave Theory and Techniques, 52(8): 1957-1963, Aug. 2004.
Copty et al. "Low-Power Near-Field Microwave Applicator for Localized Heating of Soft Matter", Applied Physics Letters, 84(25): 5109-5111, Jun. 21, 2004.
Damianou et al. "Dependence of Ultrasonic Attenuation and Absorpteion in Dog Soft Tissues on Temperature and Thermal Dose", Journal of the Acoustical Society of America, 102(1): 628-634, Jul. 1997.
Davies et al. "First-in-Man Safety Evaluation of Renal Denervation for Chronic Systolic Heart Failure: Primary Outcome From REACH-Pilot Study", International Journal of Cardiology, 162: 189-192, 2013.
De Man et al. "Bisoprolol Delays Progression Towards Right Heart Failure in Experimental Pulmonary Hypertension", Circulation Heart Failure, 5(1): 97-105, Published Online Dec. 9, 2011.
De Man et al. "Neurohormonal Axis in Patients With Pulmonary Arterial Hypertension. Friend or Foe?", American Journal of Respiratory and Critical Care Medicine, 187(1): 14-19, Published Online Nov. 9, 2012.
Deneke et al. "Histopathology of Intraoperatively Induced Linear Radiofrequency Ablation Lesions in Patients With Chronic Atrial Fibrillation", European Heart Journal, 26: 1797-1803, 2005.
Dewhirst et al. "Basic Principles of Thermal Dosimetry and Thermal Thresholds for Tissue Damage From Hyperthermia", International Journal of Hyperthermia, 19(3): 267-294, May-Jun. 2003.
DiBona "Neural Control of Renal Function: Cardiovascular Implications", Hypertension, 13: 539-548, 1989.
DiBona "Neural Control of the Kidney: Past, Present, and Future", Hypertension, 41: 621-624, Dec. 16, 2002.
DiBona "Physiology in Perspective: The Wisdom of the Body. Neural Control of the Kidney", American Journal of Physiology, Regulatory, Integrative and Comparative Physiology, 289(3): R633-R641, Sep. 2005.

(56) References Cited

OTHER PUBLICATIONS

DiBona et al. "Differentiated Sympathetic Neural Control of the Kidney", American Journal of Physiology, 271: R84-R90, 1996.
DiBona et al. "Translational Medicine: The Antihypertensive Effect of Renal Denervation", American Journal of Physiology, Regulatory, Integrative and Comparative Physiology, 298(2): R245-R253, Feb. 2010.
Diederich et al. "Catheter-Based Ultrasound Applicators for Selective Thermal Ablation: Progress Towards MRI-Guided Applications in Prostate", International Journal of Hyperthermia, 20(7): 739-756, Nov. 2004.
Diederich et al. "Catheter-Based Ultrasound Devices and MR Thermal Monitoring for Conformal Prostate Thermal Therapy", 30th Annual International IEEE EMBS Conference, Vancouver, British Columbia, Canada, Aug. 20-24, 2008, p. 3664-3668, 2008.
Diederich et al. "Induction of Hyperthermia Using An Intracavitary Multielement Ultrasonic Applicator", IEEE Transactions on Biomedical Engineering, 36(4): 432-438, Apr. 1989.
Diederich et al. "Ultrasound Technology for Hyperthermia", Ultrasound in Medicine & Biology, 25(6): 871-887, 1999.
Donoho et al. "Stable Recovery of Sparse Overcomplete Representations in the Presence of Noise", IEEE Transactions on Information Theory, 52(1): 1-42, Jan. 2006.
Drake et al. "Problematic Anatomical Sites Around the Pulmonary Artery", Gray's Anatomy for Students, 9 P., 2004.
Esler "The 2009 Carl Ludwig Lecture: Pathophysiology of the Human Sympathetic Nervous System in Cardiovascular Diseases: The Transition From Mechanisms to Medical Management", Journal of Applied Physiology, 108: 227-237, 2010.
Esler et al. "Measurement of Total and Organ-Specific Norepinephrine Kinetics in Humans", American Journal of Physiology—Endocrinology Metabolism 10, 247(1/Pt.1): E21-E28, Jul. 1984.
Esler et al. "Renal Sympathetic Denervation for Treatment of Drug-Resistant Hypertension: One-Year Results From the Symplicity HTN-2 Randomized, Controlled Trial", Circulation, 126: 2976-2982, 2012.
Failla et al. "Sympathetic Tone Restrains Arterial Distensibility of Healthy and Atherosclerotic Subjects", Journal of Hypertension, 17: 1117-1123, 1999.
Fischell PeriVascular Renal Denervation (PVRD™), Ablative Solutions Inc., TransCatheter Therapeutics Meeting, Miami, FL, USA, Oct. 24, 2012, PowerPoint Presentation, 14 P., Oct. 2012.
Fort Wayne Metals "HHS Tube", Fort Wayne Metals Research Products Corporation, 2 P., 2009.
Fujikura et al. "Effects of Ultrasonic Exposure Parameters on Myocardial Lesions Induced by High-Intensity Focused Ultrasound", Journal of Ultrasound Medicine, 25: 1375-1386, 2006.
Galie et al. "2015 ESC/ERS Guidelines for the Diagnosis and Treatment of Pulonary Hypertension. The Joint Task Force for the Diagnosis and Treatment of Pulmonary Hypertension of the European Society of Cardiology (ESC) and the European Respiratory Society (ERS). Endorsed by: Association for European Paediatric and Congenital Cardiology (AEPC), International Society for Heart and Lung Transplantation (ISHLT)", European Heart Journal, 37(1): 67-119, Published Online Aug. 29, 2015.
Galie et al. "New Treatment Stategies for Pulmonary Arterial Hypertension. Hopes or Hypes?", Journal of the American College of Cardiology, 62(12): 1101-1102, Sep. 17, 2013.
Galie et al. "Updated Treatment Algorithm of Pulmonary Arterial Hypertension", Journal of the American College of Cardiology, 62(25/Suppl.D): D60-D72, 2013.
Gander et al. "Least-Squares Fitting of Circles and Ellipses", BIT Numerical Mathematics, 34(4): 558-578, Dec. 1994.
Giering et al. "Determination of the Specific Heat Capacity of Healthy and Tumorous Human Tissue", Thermochimica Acta, 251: 199-205, Mar. 1995.
Glazier et al. "Laser Balloon Angioplasty Combined With Local Intrcoronary Heparin Therapy: Immediate and Short-Term Follow-Up Results", American Heart Journal, 134: 266-273, 1997.
Goswami "Renal Denervation: A Percutaneous Therapy for HTN", Prairie Heart Institute, Synvacor, The VEINS: Venous Endovascular Interventions Strategies, Chicago, USA, 42 P., 2012.
Granada et al. "A Translational Overview for the Evaluation of Peri-Renal Denervation Technologies", Cardiovascular Research Foundation, Columbai University Medical Center, New York, USA, Alizee Pathology, 25 P., 2011.
Grassi et al. "Sympathetic Mechanisms, Organ Damage, and Antihypertensive Treatment", Current Hypertension Report, 13: 303-308, 2011.
Griffiths et al. "Thoraco-Lumbar Splanchnicectomy and Sympathectomy. Anaesthetic Procedure", Anaesthesia, 3(4): 134-146, Oct. 1948.
Grimson et al. "Total Thoracic and Partial to Total Lumbar Sympathectomy, Splanchnicectomy and Celiac Ganglionectomy for Hypertension", Annals of Surgery, 138(4): 532-547, Oct. 1953.
Heath et al. "The Structure of the Pulmonary Trunk at Different Ages and in Cases of Pulmonary Hypertension and Pulmonary Stenosis", The Journal of Pathology and Bacteriology, 77(2): 443-456, Apr. 1959.
Hering et al. "Renal Denervation in Moderate to Severe CKD", Journal of the American Society of Nephrology, 23: 1250-1257, 2012.
Hering et al. "Substantial Reduction in Single Sympathetic Nerve Firing After Renal Denervation in Patients With rRsistant Hypertension", Hypertension, 61: 1-14, Nov. 19, 2012.
Holdaas et al. "Modulation of Reflex Renal Vasoconstriction by Increased Endogenous Renal Prostaglandin Synthesis", The Journal of Pharmacology and Experimental Therapeutics, 232(3): 725-731, 1985.
Humbert et al. "Advances in Therapeutic Interventions for Patients With Pulmonary Arterial Hypertension", Circulation, XP055531396, 130(24): 2189-2208, Published Online Dec. 9, 2014.
Janssen et al. "Role of Afferent Renal Nerves in Spontaneous Hypertension in Rats", Hypertension, 13: 327-333, 1989.
Joner "Histopathological Characterization of Renal Arteries After Radiofrequency Catheter Based Sympathetic Denervation in a Healthy Porcine Model", Deutsches Herzzentrum M?nchen, Technische Universit?t M?nchen, PowerPoint Presentation, TCT 2012, 15 P., 2012.
Katholi "Renal Nerves in the Pathogenesis of Hypertension in Experimental Animals and Humans", American Journal of Physiology, 245: F1-F14, 1983.
Katholi et al. "Intrarenal Adenosine Produces Hypertension by Activating the Sympathetic Nervous System Via the Renal Nerves in the Dog", Journal of Hypertension, 2: 349-359, 1984.
Katholi et al. "Renal Nerves in the Maintenance of Hypertension: A Potential Therapeutic Target", Current Hypertension Reports, 12(3): 196-204, Jun. 2010.
Kleinlogel et al. "A Gene-Fusion Strategy for Stoichiometric and Co-Localized Expression of Light-Gated Membrane Proteins", Nature Methods, 8(12): 1083-1091, Dec. 2011.
Kline et al. "Functional Reinnervation and Development of Supersensitivity to NE After Renal Denervation in Rats", American Journal of Physiology, 238: R353- R358, 1980.
Kolh "Carotid Denervation by Adventitial Stripping: A Promising Treatment of Carotid Sinus Syndrome?", European Journal of Vascular and Endovascular Surgery, 39(2): 153-154, Feb. 2010.
Krum et al. "Catheter-Based Renal Sympathetic Denervation for Resistant Hypertension: A Multicentre Safety and Proof-of-Principle Cohort Study", The Lancet, 373: 1275-1281, Apr. 11, 2009.
Krum et al. "Catheter-Based Renal Sympathetic Denervation for Resistant Hypertension: A Multicentre Safety and Proof-of-Principle Cohort Study", The Lancet, 373: 1275-1281, Mar. 30, 2009.
Kummer "Pulmonary Vascular Innervation and Its Role in Responses to Hypoxia: Size Matters!", Proceedings of the American Thoracic Society, 8(6): 471-476, Nov. 1, 2011.
Lafon "Miniature Devices for Minimally Invasive Thermal Ablation by High Intensity Ultrasound", Cargese Workshop 2009, University of Lyon, France, Inserm U556, Presentation, 39 P., 2009.

(56) References Cited

OTHER PUBLICATIONS

Lambert et al. "Redo of Percutaneous Renal Denervation in a Patient With Recurrent Resistant Hypertension After Primary Treatment Success", Catheterization and Cardiovascular Interventions, p. 1-11, 2012.
Lele "Effects of Focused Ultrasonic Radiation on Peripheral Nerve, With Observations on Local Heating", Experimental Neurology, 8: 47-83, 1963.
Lemoine et al. "Amputations and Sympathectomy in Peripheral Vascular Disease of the Lower Extremity. Experience With 180 Patients", Journal of the National Medical Association, 61(3): 219-221, May 1969.
Li et al. "Acoustic Proximity Ranging in the Presence of Secondary Echoes", IEEE Transactions on Instrumentation and Measurement, XP011102759, 52(5): 1593-1605, Oct. 1, 2003. p. 1593.
Lin et al. "Utility of the PlasmaKinetic™ Bipolar Forceps® for Control of the Renal Artery in a Porcine Model", JTUA, 14(3): 118-121, Sep. 2003.
Liu et al. "A Helical Microwave Antenna for Welding Plaque During Balloon Angioplasty", IEEE Transactions on Microwave Theory and Techniques, 44(10): 1819-1831, Oct. 1996.
Liu et al. "Pulmonary Artery Denervation Improves Pulmonary Arterial Hypertension Induced Right Ventricular Dysfunction by Modulating the Local Renin-Angiotensin-Aldosterone System", BMC Cardiovascular Disorders, 16(1): 192-1-192-10, Oct. 10, 2016.
Lopez et al. "Effects of Sympathetic Nerves on Collateral Vessels in the Limb of Atherosclerosis Primates", Atherosclerosis, 90: 183-188, 1991.
Mabin et al. "First Experience With Endovascular Ultrasound Renal Denervation for the Treatment of Resistant Hypertension", EuroIntervention, 8: 57-61, 2012.
Mahfoud et al. "Effect of Renal Sympathetic Denervation on Glucose Metabolism in Patients With Resistant Hypertension: A Pilot Study", Circulation, 123: 1940-1946, 2011.
Mahfoud et al. "Is There A Role for Renal Sympathetic Denervation in the Future Treatment of Resistant Hypertension?", Future Cardiology, 7(5): 591-594, 2011.
Mahfoud et al. "Renal Hemodynamics and Renal Function After Catheter-Based Renal Sympathetic Denervation in Patients With Resistant Hypertension", Hypertension, 60: 419-424, 2012.
Makris et al. "Resistant Hypertension Workup and Approach to Treatment", International Journal of Hypertension, 2011(Art. ID598694): 1-10, 2011.
Manasse et al. "Clinical Histopathology and Ultrstructural Analysis of Myocardium Following Microwave Energy Ablation", European Journal of Cardio-Thoracic Surgery, 23: 573-577, 2003.
Mangoni et al. "Effect of Sympathectomy on Mechanical Properties of Common Carotid and Femoral Arteries", Hypertension, 30: 1085-1088, 1997.
Martin et al. "Premise, Promise, and Potential Limitations of Invasive Devices to Treat Hypertension", Current Cardiology Reports, 13(1): 86-92, Feb. 2011.
Mazor "Efficacy of Renal Denervation Is Positively Impacted by Longitudinal Treatments", Vessix Vascular Inc., PowerPoint Presentation, TCT 2012, 20 P., 2012.
MERIT-HF Study Group "Effect of Metaprolol CR/XL in Chronic Heart Failure: Metoprolol CR/XL Randomised Intervention Trial in Congestive Heart Failure (MERIT-HF)", The Lancet, 353(9169): 2001-2007, Jun. 12, 1999.
Mogil et al. "Renal Innervation and Renin Activity in Salt Metabolism and Hypertension", American Journal of Physiology, 216(4): 693-697, Apr. 1969.
Moretti et al. "Beta Blocker for Patients With Pulmonary Arterial Hypertension: A Single Center Experience", International Journal of Cardiology, 184(1): 528-532, Available Online Feb. 24, 2015.
Mortensen et al. "Catheter-Based Renal Sympathetic Denervation Improves Central Hemodynamics and Arterial Stiffness: A Pilot Study", The Journal of Clinical Hypertension, 14(12): 861-870, Dec. 2012.
Nootens et al. "Neurohormonal Activation in Patients With Right Ventricular Failure From Pulmonary Hypertension: Relation to Hemodynamic Variables and Endothelin Levels", Journal of the American College of Cardiology, JACC, 26(7): 1581-1585, Dec. 1995.
Ohkubo et al. "Histological Findings After Angioplasty Using Conventional Balloon, Radiofrequency Thermal Balloon, and Stent for Experimental Aortic Coarctation", Pediatrics International, 46: 39-47, 2004.
Olafsson et al. "Ultrasound Current Source Density Imaging", IEEE Transactions on Biomedical Engineering, 55(7): 1840-1848, Jul. 2008.
Ong et al. "Successful Treatment of Resistant Hypertension With Percutaneous Renal Denervation Therapy", Heart, 98(23): 1754-1755, Dec. 2012.
Ormiston "OneShot (Covidien)", Maya Medical, Auckland, New Zealand, PowerPoint Presentation.
Ormiston et al. "First-in-Human Use of the OneShot™ M Renal Denervation System From Covidien", EuroIntervention, 8: 1090-1094, 2013.
Packer et al. "Effect of Carvedilol on Survival in Severe Chronic Heart Failure", The New England Journal of Medicine, 344(22): 1651-1658, May 31, 2001.
Page et al. "The Effect of Renal Denervation on Patients Suffering From Nephritis", The Journal of Clinical Investigation, 14(4): 443-458, Jul. 1935.
Papademetriou et al. "Renal Sympathetic Denervation for the Treatment of Difficult-to-Control or Resistant Hypertension", International Journal of Hypertension, 2011(Art.ID196518): 1-8, Jan. 2011.
Para Tech Coating "Parylene Properties", Para Tech Coating Inc., 1 P., 2010.
Perros et al. "Nebivolol for Improving Endothelial Dysfunction, Pulmonary Vascular Remodeling, and Right Heart Function in Pulmonary Hypertension", Journal of the American College of Cardiology, JACC, 65(7): 668-680, Feb. 24, 2015.
Pokushalov et al. "A Randomized Comparison of Pulmonary Vein Isolation With Versus Without Concomitant Renal Artery Denervation in Patients With Refractory Symptomatic Atrial Fibrillation and Resistant Hypertension", Journal of the American College of Cardiology, 60(13): 1163-1170, 2012.
Prapa et al. "Histopathology of the Great Vessels in Patients With Pulmonary Arterial Hypertension in Association With Congenital Heart Disease: Large Pulmonary Arteries Matter Too", international Journal of Cardiology, 168: 2248-2254, Available Online Feb. 28, 2013.
Prochnau et al. "Catheter-Based Renal Denervation for Drug-Resistant Hypertension by Using a Standard Electrophysiology Catheter", EuroIntervention, 7: 1077-1080, 2012.
Prochnau et al. "Efficacy of Renal Denervation With a Standard EP Catheter in the 24-h Ambulatory Blood Pressure Monitoring—Long-Term Follow-Up", International Journal of Cardiology, 157(3): 447-448, Jun. 14, 2012.
Qin "Physician's Prescription Manual", Wen-han, Qin: 590, People's Military Medical Press, Feb. 1998 with Machine Translation.
Quinn "Pre-Eclampsia and Partial Uterine Denervation", Medical Hypotheses, 64(3): 449-454, 2005. Abstract.
Rappaport "Treating Cardiac Disease With Catheter-Based Tissue Heating", IEEE Microwave Magazine, p. 57-64, Mar. 2002.
Reddy "Sound Intervention", Mount Sinai School of Medicine, MSSM, Presentation, 19 P., 2012.
Roehl et al. "Comparison of 3 Methods to Induce Acute Pulmonary Hypertension in Pigs", Comparative Medicine, 59(3): 280-286, Jun. 2009.
Rosanio et al. "Pulmonary Arterial Hypertension in Adults: Novel Drugs and Catheter Ablation Techniques Show Promise? Systematic Review on Pharmacotherapy and Interventional Strategies", BioMed Research International, XP055754039, 2014(lArt.743868): 1-17, Jun. 12, 2014.
Rothman "FIM Evaluation of a New, Multi-Electrode RF System for Renal Denervation (Medtronic)", Medtronic Inc., PowerPoint Presentation, 8 P., 2012.
Rothman et al. "Pulmonary Artery Denervation Reduces Pulmonary Artery Pressure and Induces Histological Changes in an Acute

(56) References Cited

OTHER PUBLICATIONS

Porcine Model of Pulmonary Hypertension", Circulation: Cardiovascular Interventions, 8(11): e002569-1-e002569-7, Published Online Nov. 17, 2015.
Rousselle "Experimental Pathways for the Evaluation of Extrinsic Renal Nerve Distribution, Density, and Quantification (Swine Model)", Alizee Pathology in Collaboration With Jack Skirkball Center for Cardiovascular Research, TCT, 20 P., Nov. 8, 2011.
Rousselle "Renal Artery Dervation: Experimental Pathways for the Evaluation of Extrinsic Renal Nerve Distribution, Density, and Quantification (Swine Model)", Alizee Pathology, Cardiovascular Research Foundation, Nov. 8, 2011.
Sakakura et al. "Methodological Standardization for the Pre-Clinical Evaluation of Renal Sympathetic Denervation", JACC: Cardiovascular Interventions. 7(10): 1184-1193, Published Online Sep. 14, 2014.
Sangiorgi et al. "Histo-Morphometric Evaluation of 2D Characteristics and 3D Sympatetic Renal Nerve Distribution in Hypertensive Vs. Normotensive Patients", Department of Pathology, Department of Cardiology, University of Rome Tor Vergata, Department of Cardiology University of Modena and Reggio Emilia, Medtronic Cardiovascular, PowerPoint Presentation, TCT 2012, 22 P., 2012.
Sanni et al. "Is Sympathectomy of Benefit in Critical Leg Ischaemia Not Amenable to Revascularisation?", Interactive Cardio Vascular and Thoracic Surgery, 4: 478-483, 2005.
Scheinert "Cardiosonic Tivus™ Technology: An Intra-Vascular Ultrasonic Catheter for Targeted Renal Denervation", Center for Vascular Medicine, Park Hospital Leipzig, Germany, PowerPoint Presentation, TCT 2012, 16 P., 2012.
Schelegle et al. "Vagal Afferents Contribute to Exacerbates Airway Responses Following Ozone and Allergen Challenge", Respiratory Physiology & Neurobiology, 181(3): 277-285, May 31, 2012.
Schlaich "Long-Term Follow Up of Catheter-Based Renal Denervation for Resistant Hypertension Confirms Durable Blood Pressure Reduction", Hypertension & Kidney Disease Laboratory, Baker IDI Heart & Diabetes Institute, Melbourne VIC, Australia, PowerPoint Presentation, TCT 2012, 22 P., 2012.
Schlaich et al. "Renal Sympathetic-Nerve Ablation for Uncontrolled Hypertension", New England Journal of Medicine, 361(9): 932-934, Aug. 27, 2009.
Schnyder et al. "Common Femoral Artery Anatomy Is Influenced by Demographics and Comorbidity: Implications for Cardiac and Peripherial Invasive Studies", Catheterization and Cardiovascular Interventions, 53(3): 289-295, Jul. 2001.
Schwartz "Strategies to Model Efficacy of Hypertension Devices", EuroPCR 2013, The Leading Cardiovascular Course, 24 P., 2013.
Shelton Jr. et al. "A Nondestructive Technique to Measure Pulmonary Artery Diameter and Its Pulsatile Variations", Journal of Applied Physiology, 33(4): 542-544, Oct. 1972.
Shung "Doppler Flow Measurements", Diagnostic Ultrasound—Imaging and Blood Flow Measurements, Chap.5:103-104, 2006.
Sievert et al. "Catheter-Based Technology Alternatives for Renal Denervation", CardioVascular Center Frankfurt, Germany, TCT 2012, Miami, FL, USA, Oct. 22-26, 2012, PowerPoint Presentation, 35 P., Oct. 2012.
Simonneau et al. "Updated Clinical Classification of Pulmonary Hypertension", Journal of the American College of Cardiology, 54(1/Suppl.S): S43-S54, Jun. 30, 2009.
Sitbon et al. "Beyond a Single Pathway: Combination Therapy in Pulmonary Arterial Hypertension", European Respiratory Review, 25(142): 408-417, Dec. 2016.
SOLVD Investigators "Effect of Enalapril on Survival in Patients With Reduced Left Ventricular Ejection Fractions and Congestive Heart Failure", The New England Journal of Medicine, 325(5): 293-302, Aug. 1, 1991.
Souchon et al. "Monitoring the Formation of Thermal Lesions With Heat-Induced Echo-Strain Imaging: A Feasibility Study", Ultrasound in Medicine & Biology, 31(2): 251-259, 2005.

Stefanadis "Vincristine Local Delivery for Renal Artery Denervation", Athens, Greece, PowerPoint Presentation, TCT 2012, 21 P., 2012.
Steigerwald et al. "Morphological Assessment of Renal Arteries After Radiofrequency Catheter-Based Sympathetic Denervation in a Porcine Model", Journal of Hypertension, 30(11): 2230-2239, Nov. 2012.
Swierblewska et al. "An Independent Relationship Between Muscle Sympathetic Nerve Activity and Pulse Wave Velocity in Normal Humans", Journal of Hypertension, 28: 979-984, 2010.
Symplicity HTN-1 Investigators "Catheter-Based Renal Sympathetic Denervation for Resistant Hypertension: Durability of Blood Pressure Reduction Out to 24 Months", Hypertension, 57: 911-917, Mar. 14, 2011.
Symplicity HTN-2 Investigators "Renal Sympathetic Denervation in Patients With Treatment-Resistant Hypertension (The Symplicity HTN-2 Trial): A Randomised Controlled Trial", The Lancet, 376(9756): 1903-1909, Published Online Nov. 17, 2010.
Symplicity HTN-2 Investigators "Renal Sympathetic Denervation in Patients With Treatment-Resistant Hypertension (The Symplicity HTN-2 Trial): A Randomised Controlled Trial", The Lancet, 376: 1903-1909, Dec. 4, 2010.
Szabo "Diagnostic Ultrasound Imaging Inside Out", Academic Press Series in Biomedical Engineering, 2004.
Techavipoo et al. "Temperature Dependence of Ultrasonic Propagation Speed and Attenuation in Excised Canine Liver Tissue Measured Using Transmitted and Reflected Pulses", Journal of the Acoustical Society of America, 115(6): 2859-2865, Jun. 2004.
Thenappan et al. "Beta-Blocker Therapy Is Not Associated With Adverse Outcomes in Patients With Pulmonary Arterial Hypertension. A Propensity Score Analysis", Circulation Heart Failure, 7(6): 903-910, Published Online Oct. 2, 2014.
Tibshirani "Regression Shrinkage and Selction Via the Lasso: A Retrospective", Journal of the Royal Statistical Society, Series B: Statistical Methodology, 73(Pt.3): 273-282, 2011.
Tibshirani "Regression Shrinkage and Selection Via the Lasso", Journal of the Royal Statistical Society, Series B: Methodological, 58(1): 267-288, 1996.
Toorop et al. "Clinical Results of Carotid Denervation by Adventitial Stripping in Caotid Sinus Syndrome", Europan Journal of Vascular and Endovascular Syndrome, 39: 146-152, 2010.
Tyreus et al. "Two-Dimensional Acoustic Attenuation Mapping of High-Temperature Interstitial Ultrasound Lesions", Physics in Medicine and Biology, 49: 533-546, 2004.
Van Albada et al. "Biological Serum Markers in the Managment of Pediatric Pulmonary Arterial Hypertension", Pediatric Research, 63(3): 321-327, Mar. 2008.
Van Campen et al. "Bisoprolol in Idiopathic Pulmonary Arterial Hypertension: an Explorative Study", European Respiratory Journal, 48: 787-796, 2016.
Velez-Roa et al. "Increased Sympathetic Nerve Activity in Pulmonary Artery Hypertension", Circulation, 110(10): 1308-1312, Sep. 7, 2004.
Verloop et al. "The Effects of Renal Denervation on Renal Haemodynamics", Interventions for Hypertenison & Heart Failure, Abstracts of EuroPCR & AsiaPCR/SingLive 2013, May 21, 2013.
Virmani "Translation Medicine and Renal Denervation: Pre-Clinical Animal Models and Histoanatomy", CVPath Institute, Gaithersburg, MD, USA, PowerPoint Presentation.
Voskuil et al. "Percutaneous Renal Denervation for the Treatment of Resistant Essential Hypertension; The First Dutch Experience", Netherlands Heart Journal, 19(7-8): 319-323, Aug. 2011.
Warwick et al. "Trackless Lesions in Nervous Tissues Produced by High Intensity Focused Ultrsound (High-Frequency Mechanical Waves)", Journal of Anatomy, 102(3): 387-405, 1968.
Wei-Feng "New Theories and New Technologies for Cardiovascular Diseases", People's Military Medical Press, 324: 3P., 2015. ( Chinese only).
Wikswo Jr. et al. "Magnetic Field of a Nerve Impulse: First Measurements", Science, 208: 53-55, Apr. 4, 1980.
Wilcox "Resistant Hypertension and the Role of the Sympathetic Nervous System", Medtronic, 30 P.

(56) References Cited

OTHER PUBLICATIONS

Williams et al. "Laser Energy Source in Surgical Atrial Fibrillation Ablation: Preclinical Experience", The Annals of Thoracic Surgery, 82: 2260-2264, 2006.
Witkowski "Future Perspective in Renal Denervation: Congestive Heart Failure, Insulin Resistance and Sleep Apnea", Innovations in Cardiovascular Interventions, ICI Meeting 2011, Tel Aviv, Israel, Dec. 4-6, 2011, 23 P., 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58(4): 559-565, Oct. 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58: 559-565, Aug. 15, 2011.
Witte et al. "Imaging Current Flow in Lobster Nerve Cord Using the Acoustoelectric Effect", Applied Physics Letters, 90: 163902-1-163902-3, 2007.
Wolf-De Jonge et al. "25 Years of Laser Assisted Vascular Anastomosis (LAVA): What Have We Learned?", European Journal of Vascular and Endovascular Surgery, 27(5): 466-476, May 2004.
Worthington et al. "Changes in Ultrasound Properties of Porcine Kidney Tissue During Heating", Ultrasound in Medicine & Biology, 27(5): 673-682, 2001.
Worthington et al. "Ultrasound Properties of Human Prostate Tissue During Heating", Ultrsound in Medicine & Biology, 28(10): 1311-1318, 2002.
Wright "On a Relationship Between the Arrhenius Parameters From Thermal Damage Studies", Transactions of the ASME, Technical Brief, Journal of Biomechanical Engineering, 125(2): 300-304, Apr. 9, 2003.
Wu et al. "A Quality Control Program for MR-Guided Focused Ultrasound Ablation Therapy", Journal of Applied Clinical Medical Physics, 3(2): 162-167, Spring 2002.
Wu et al. "Noninvasive Cardiac Arrhythmia Therapy Using High-Intensity Focused Ultrasound (HIFU) Ablation", International Journal of Cardiology, 166(2): e28-e30, Available Online Feb. 26, 2013.
Xu et al. "Experimental Nerve Thermal Injury", Brain, 117: 375-384, 1994.
Zeller "Percutaneous Renal Denervation System. The New Ultrasound Solution for the Mangament of Hypertension", Paradise Ultrasound Denervation System, ReCor Medical, 27 P., 2013.
Zhang et al. "Pulmonary Arterial Hypertension: Pharmacologic Therapies and Potential Pulmonary Artery Denervation Treatment", EuroIntervention, XP009524288, 9(Suppl.R): R149-R154, May 2013.
Zhou et al. "Pulmonary Artery Denervation Attenuates Pulmonary Arterial Remodeling in Dogs With Pulmonary Arterial Hypertension Induced by Dehydrogenized Monocrotaline", JACC: Cardiovascular Interventions, 8(15): 2013-2023, Dec. 28, 2015.
Official Action Dated Nov. 14, 2023 from the US Patent and Trademark Office Re. U.S. Appl. No. 17/187,813. (15 pages).
Interview Summary Dated May 1, 2024 from the US Patent and Trademark Office Re. U.S. Appl. No. 16/494,322. (2 pages).
Interview Summary Dated Jul. 26, 2024 from the US Patent and Trademark Office Re. U.S. Appl. No. 16/540,191. (8 pages).
Notice of Allowance Dated Sep. 17, 2024 from the US Patent and Trademark Office Re. U.S. Appl. No. 17/752,879. (12 pages).
Notice of Allowance Dated Nov. 21, 2024 from the US Patent and Trademark Office Re. U.S. Appl. No. 17/719,412. (6 pages).
Official Action Dated Mar. 7, 2024 from the US Patent and Trademark Office Re. U.S. Appl. No. 17/719,412. (57 pages).
Official Action Dated Dec. 11, 2024 from the US Patent and Trademark Office Re. U.S. Appl. No. 16/540,191. (25 pages).
Official Action Dated Jan. 24, 2024 From the US Patent and Trademark Office Re. U.S. Appl. No. 16/439,816. (16 Pages).
Official Action Dated Jan. 24, 2024 From the US Patent and Trademark Office Re. U.S. Appl. No. 17/752,879. (15 pages).
Official Action Dated Jan. 26, 2024 from the US Patent and Trademark Office Re. U.S. Appl. No. 16/540,191. (20 pages).
Official Action Dated Aug. 28, 2024 from the US Patent and Trademark Office Re. U.S. Appl. No. 16/494,322. (50 pages).

\* cited by examiner

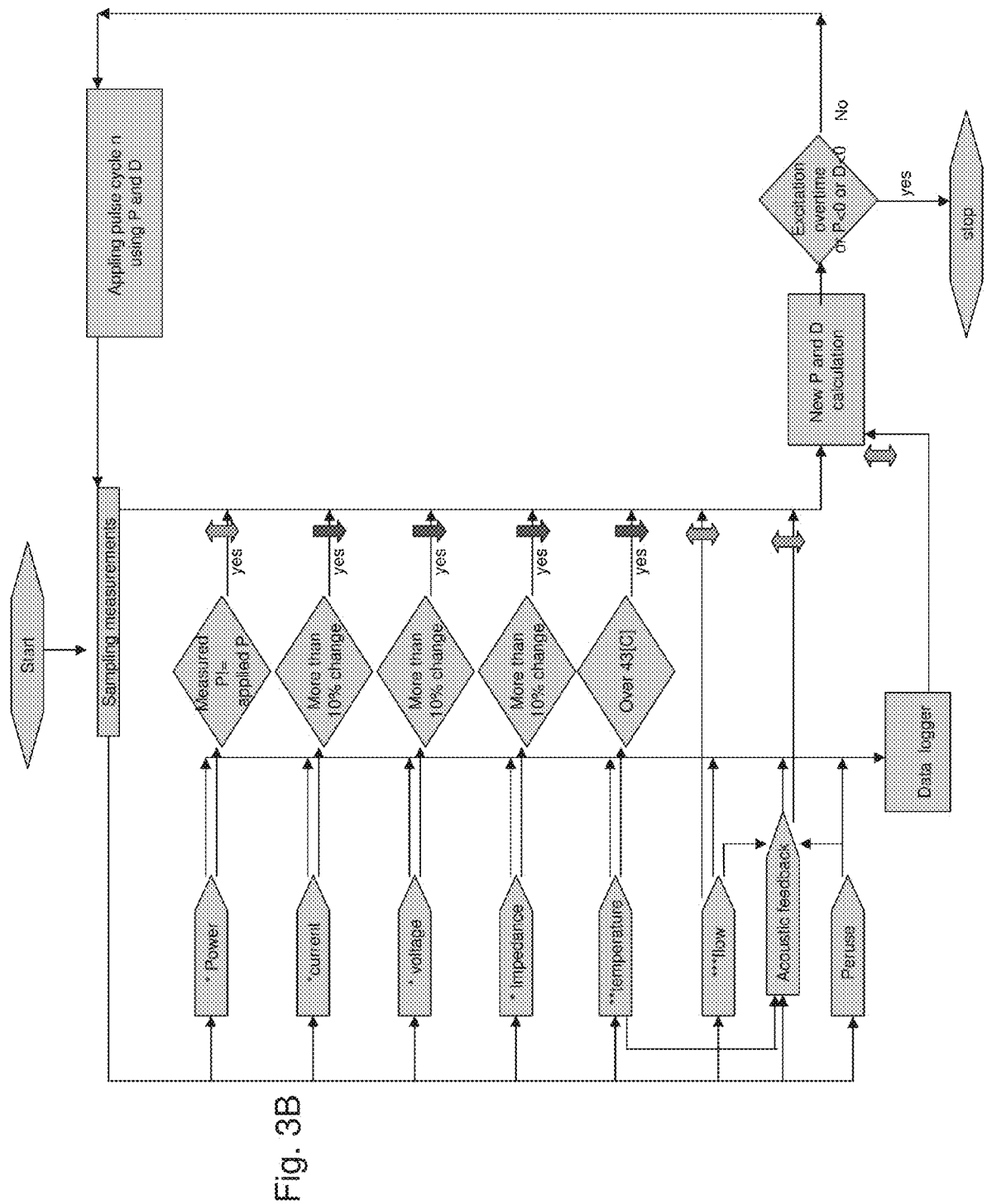

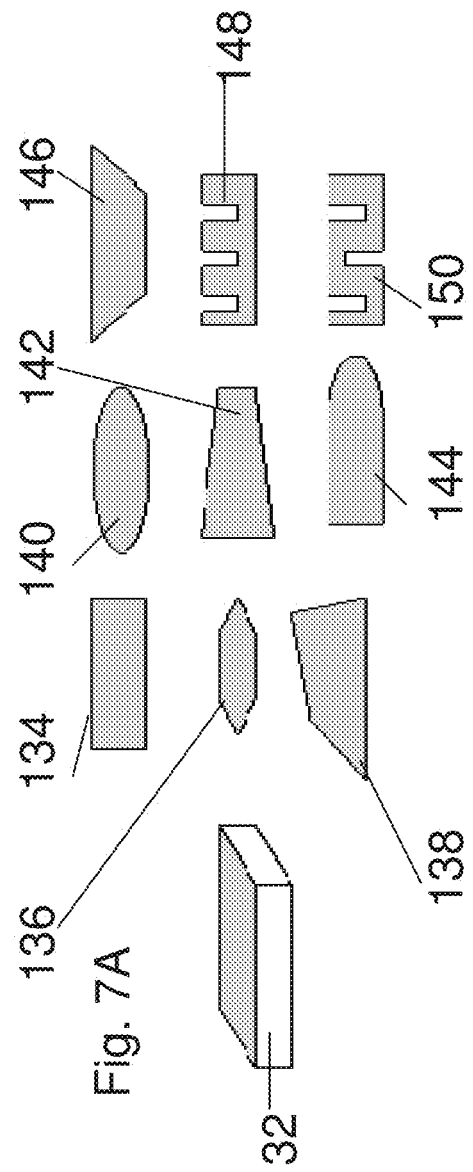
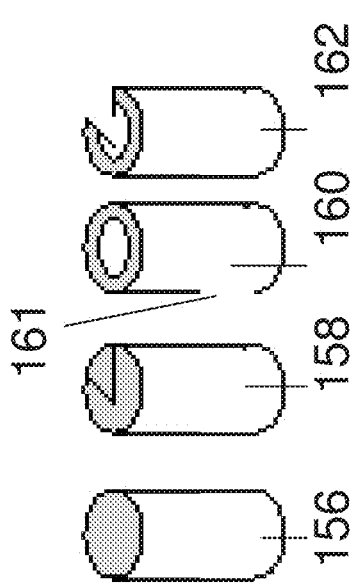

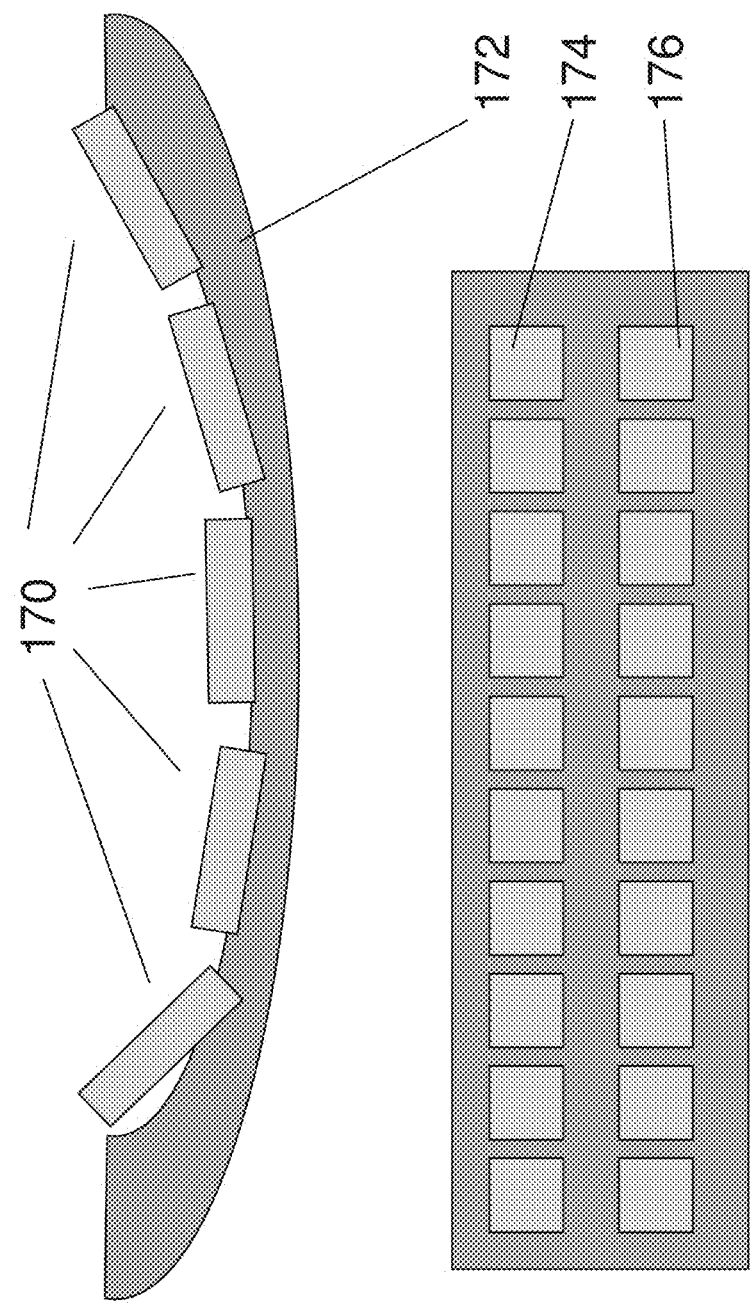

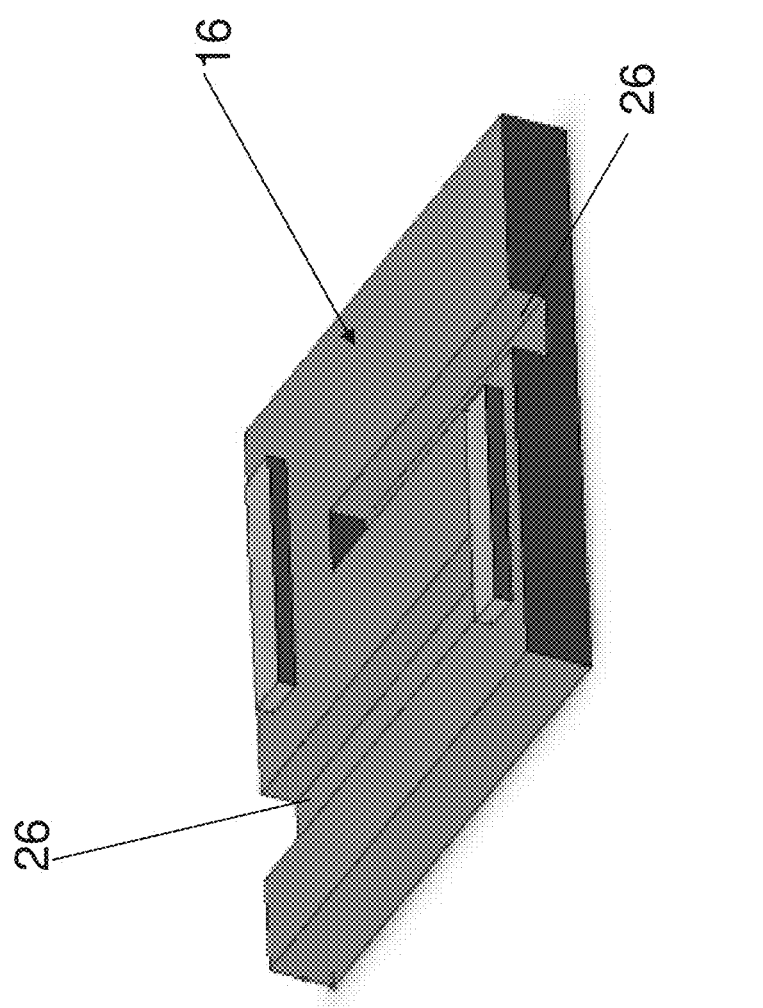

ULTRASOUND TRANSDUCER AND USES THEREOF

RELATED APPLICATIONS

This application is a continuation of U.S. patent application Ser. No. 16/451,087, filed on Jun. 25, 2019, which is a continuation of U.S. patent application Ser. No. 14/190,113 filed on Feb. 26, 2014, now U.S. Pat. No. 10,368,893, which is a division of U.S. patent application Ser. No. 13/049,013 filed on Mar. 16, 2011, now U.S. Pat. No. 8,696,581, which claims the benefit of priority under 35 USC 119(e) of U.S. Provisional Patent Application No. 61/393,947 filed on Oct. 18, 2010. The contents of the above applications are all incorporated by reference as if fully set forth herein in their entirety.

FIELD AND BACKGROUND OF THE INVENTION

The present invention relates to an ultrasound transducer device and uses thereof and, more particularly, but not exclusively to such a transducer device modified for use in surgical procedures.

Sverdlik et al, in PCT/IL2008/000234, filed Feb. 21, 2008 disclose a method of using ultrasonic energy for surgical procedures. In a procedure for stabilizing blood vessel wall abnormality, ultrasonic heating is carried out of at least a portion of the blood vessel wall having the abnormality. A parameter is monitored relating to a property of at least a portion of the heated portion of the blood vessel wall; and heating is stopped when the monitored parameter changes by a predetermined factor or after the monitored parameter changes at a slow enough rate.

A problem arises in providing the ultrasound transducer close to the tissue that requires the procedure. It is known to put small ultrasound sensors in the blood vessels but it is difficult to ensure that the sensor is looking at the tissue that requires the procedure. A further problem involves providing the ultrasound power beam sufficiently close to the tissue requiring ablation, and controlling the beam given a) the difficulty in correctly directing the sensor and b) generally controlling factors that affect efficiency of the ablation beam.

SUMMARY OF THE INVENTION

The present embodiments may provide a transducer in which sensing and ablation are combined on a single transducer device that can be placed in a blood vessel or the like.

According to one aspect of the present invention there is provided a dual use ultrasonic transducer device for combined sensing and power transmission, the power transmission for tissue ablation, comprising:
  a first piezoelectric transducer sized for placement in a body lumen;
  a power unit enabling an ultrasonic power beam for tissue ablation in a tissue ablation region; and
  a sensing unit enabling an ultrasonic sensing beam for sensing at said tissue ablation region.

In an embodiment, said first piezoelectric transducer comprises a piezoelectric surface, said piezoelectric surface being electrically connected to a mounting; the mounting comprising damping for said piezoelectric surface, the mounting being configured such as to provide a first region of said piezoelectric surface with a first relatively high level of damping and a second region of said piezoelectric surface with a second relatively low level of damping, thereby to enable said ultrasonic sensing beam from said first region and said power transmission beam from said second region.

An embodiment may comprise at least a second piezoelectric transducer also sized for placement in a body lumen, the first piezoelectric transducer being provided with a first, relatively high level of damping and the second piezoelectric transducer being provided with a second, relatively low, level of damping, and enabling said ultransonic sensing beam from said first piezoelectric transducer and said ultrasonic power beam from said second piezoelectric transducer.

In an embodiment, said ultrasonic power beam and said ultrasonic sensing beam are enabled through said first piezoelectric transducer.

In an embodiment, said body lumen is a blood vessel.

An embodiment may comprise with a catheter for placing within said blood vessel.

In an embodiment, said sensing is usable in a control system to control treatment efficacy or device efficiency.

In an embodiment, said first piezoelectric transducer is configured to provide said power transmission as a non-focused beam.

In an embodiment, said first region comprises a first surface part of said piezoelectric surface and said second region comprises a second surface part of said piezoelectric surface, and a non-focused beam is provided from throughout said second surface part.

In an embodiment, said power transmission is configured to provide a thermal effect to surrounding tissues and said sensing is configured to provide imaging of said thermal effect.

In an embodiment, said thermal effect comprises denaturation of collagen and said sensing comprises detection of a change in reflected signal, or in backscatter.

An embodiment may provide said power transmission in bursts having gaps and transmit separate sensing transmissions during said gaps.

An embodiment is configured to be placed in said body lumen and said sensing region is configured to detect a lumen wall and to provide a signal to control for distance to the lumen wall and thereby ensure that the device does not touch said lumen wall.

In an embodiment, said mounting comprises an air pocket and a plurality of contact points.

In an embodiment, said mounting is provided with a surface tension sufficient to maintain said air pocket when said device is immersed in liquid.

An embodiment may comprise a matching layer for acoustic impedance matching placed on said piezoelectric surface wherein said matching layer comprises pyrolytic graphite.

The device may have a resonance and an anti-resonance, and may advantageously be used at a working frequency equal to said anti-resonance.

According to a second aspect of the present invention there is provided a method of online testing of efficiency or treatment efficacy of an ultrasound transducer to detect changes in said efficiency, said efficiency being a ratio between ultrasound energy and heat generated in said transducer, said method comprising applying an impulse to said ultrasound transducer, measuring a response of said ultrasound transducer to said impulse, and inferring changes in said efficiency or said efficacy from said measured response.

In an embodiment, said inferring said changes in efficiency comprises inferring from at least one member of the group comprising: a shape of said measured response; an envelope of said measured response, a duration of said measured response, amplitudes of said measured response, and a damping factor of said measured response.

In an embodiment, said transducer has a resonance and an anti-resonance and said online or offline testing comprises inferring a change in at least one of said resonance and said anti-resonance.

Usage of the embodiment may involve placing said transducer in a liquid-filled body lumen and carrying out said online testing while said transducer is in said body lumen.

The embodiments extend to the device when placed in a liquid within a body lumen.

According to a third aspect of the present invention there is provided a method of using an ultrasonic transducer for simultaneous heating and monitoring of a target, the method comprising providing a relatively high power ultrasonic transmission in bursts for heating said target, said bursts having gaps, and sending relatively low power ultrasonic sensing transmissions during said gaps for monitoring said target.

An embodiment may comprise using a surface of a piezoelectric sensor to produce said relatively high power and said relatively low power ultrasonic transmissions, said piezoelectric sensor surface comprising a first relatively high damping region and a second relatively low damping region, the method comprising using said first region for said monitoring and said second region for said heating.

An embodiment may comprise placing said transducer in a liquid-filled body lumen and carrying out said simultaneous heating and measuring while said transducer is in said body lumen.

An embodiment may involve testing an efficiency of said transducer or a treatment efficacy, said testing comprising applying an impulse to said transducer and measuring a response of said transducer to said impulse.

According to a fourth aspect of the present invention there is provided a method of online testing of efficiency of an ultrasound transducer to detect changes in said efficiency, said efficiency being a ratio between ultrasound energy and heat generated in said transducer, said method comprising measuring an impedance of said transducer at a current working frequency, and inferring changes in said efficiency from changes in said measured impedance.

According to a fifth aspect of the present invention there is provided a method of online testing of efficiency of an ultrasound transducer to detect changes in said efficiency, said efficiency being a ratio between ultrasound energy and heat generated in said transducer, or for testing treatment efficacy, said transducer being for placement in a liquid flow and having a temperature sensor positioned for measurement of flowing liquid downstream of said transducer, said method comprising measuring a temperature of said flowing liquid downstream of said transducer, and inferring a decrease in said efficiency or a change in said efficacy from an increase in said measured temperature.

According to a sixth aspect of the present invention there is provided a method of online testing of treatment efficacy and safety of the device of claim 1, comprising placing the device in said lumen at a distance from a lumen wall, measuring liquid flow between the device and the wall and using changes in said flow measurement as an indicator of said treatment efficacy or said safety.

Unless otherwise defined, all technical and scientific terms used herein have the same meaning as commonly understood by one of ordinary skill in the art to which this invention belongs. The materials, methods, and examples provided herein are illustrative only and not intended to be limiting.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Implementation of the method and/or system of embodiments of the invention can involve performing or completing selected tasks manually, automatically, or a combination thereof. This refers in particular to tasks involving control of the ultrasonic system.

Moreover, according to actual instrumentation and equipment of embodiments of the method and/or system of the invention, selected tasks may be implemented by hardware, by software or by firmware or by a combination thereof using an operating system.

For example, hardware for performing selected tasks according to embodiments of the invention may be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified schematic diagram of a first embodiment of an ultrasound transducer in which sensing and ablation are combined onto a single device according to the present invention;

FIG. 2 is a simplified schematic diagram showing a modification of the transducer of FIG. 1;

FIG. 3A is a simplified flow chart illustrating a method for monitoring operation of an ultrasound transducer according to embodiments of the present invention;

FIG. 3B is a flow chart showing a method of monitoring efficacy or operation of an ultrasound transducer according to further embodiments of the present invention;

FIG. 4 is a simplified flow chart illustrating a method for ablating tissue using high power pulses, and measuring during gaps in the pulse, according to embodiments of the present invention;

FIG. 5 is a simplified schematic diagram of a system using the air-backed ultrasound transducer of FIG. 1;

FIG. 6 is a simplified schematic diagram showing a cross-section of the construction of an ultrasound transducer according to the embodiment of FIG. 1;

FIGS. 7A-7C are simplified schematic diagrams illustrating variant shapes of a piezoelectric element for the transducer of FIG. 1;

FIG. 8A is a side view of a series of piezoelectric elements mounted on a single mounting according to an embodiment of the present invention;

FIG. 8B is a view from above of an arrangement of piezoelectric elements mounted in two rows according to embodiments of the present invention;

FIG. 9 is a simplified schematic diagram illustrating a construction of a PCB for mounting PCB elements that includes grooves for air bubble formation according to an embodiment of the present invention;

Figure 10:
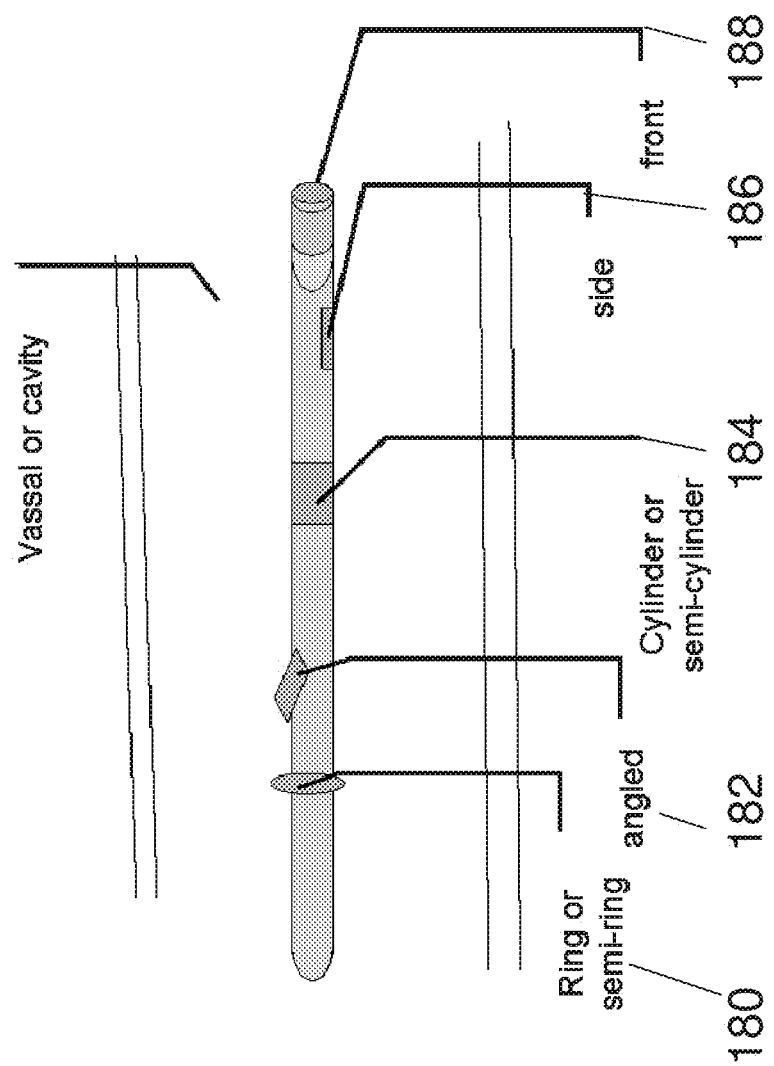
Figure 12:
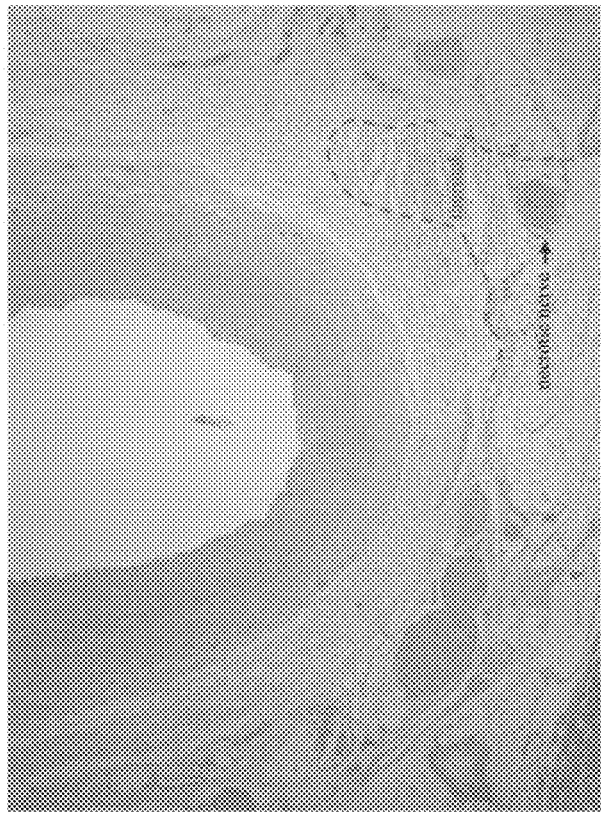
Figure 11:
Figure 14:
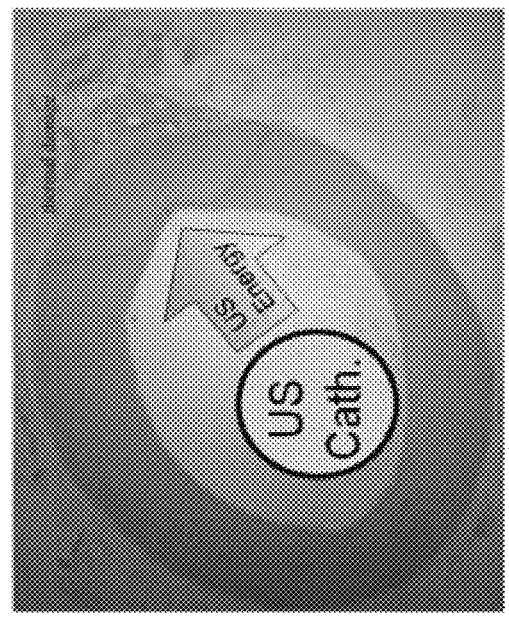
Figure 13:
Figure 15:
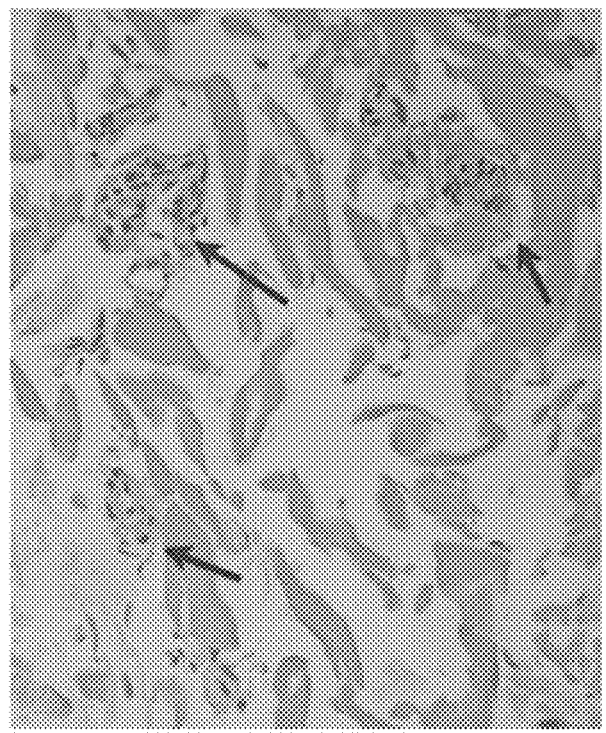
Figure 16:
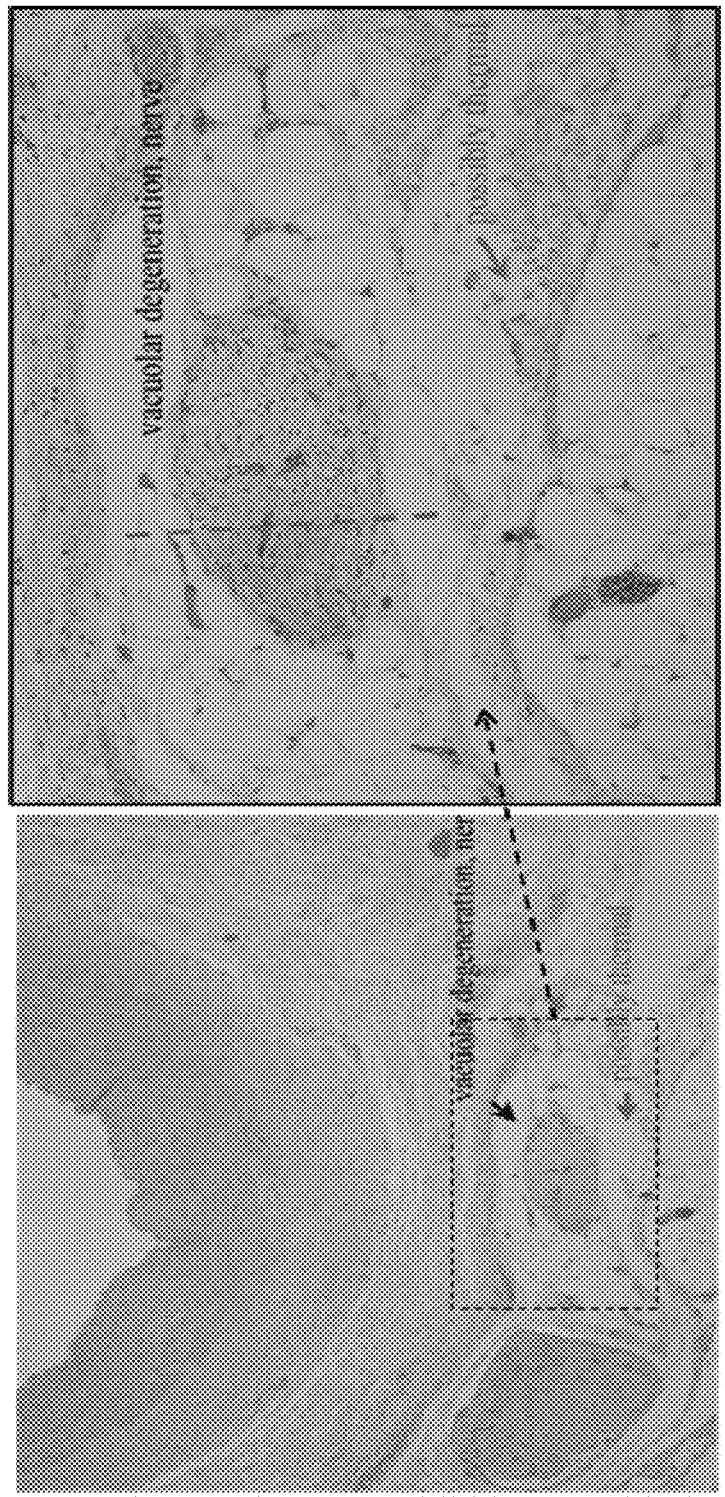

FIG. 10 is a simplified schematic diagram that illustrates a series of angles and positions in relation to a body vessel and a catheter, in which the transducer can be placed by navigation;

FIG. 11 is a histology slide using H&E stain, and showing the thermal effect in a pig carotid artery;

FIG. 12 is a histology slide using H&E stain, and showing the thermal effect in a pig renal artery;

FIG. 13 is a histology slide wherein analysis and marking of the thermal damage area to a pig Carotid Artery is made by a trained pathologist;

FIG. 14 is a histology slide wherein analysis and marking of the thermal damage area to a pig Renal Artery is made by a trained pathologist;

FIG. 15 is a histology slide showing analysis and marking of the blocked Vasa-Vasorum, with arrows placed by a trained pathologist in a pig Carotid Artery Vasa-Vasorum in the adventitia; and FIG. 16 shows two histology slides with analysis and marking of the thermal damage, or nerve degeneration area, made by trained pathologist, for a pig renal artery, and nerves in adventitia.

DESCRIPTION OF THE PREFERRED EMBODIMENTS

The present embodiments comprise an ultrasound transducer device and uses thereof and, more particularly, but not exclusively, such a transducer device modified for use in surgical procedures. The transducer device combines imaging and ablation into a single device.

The single device may include multiple transducers or a single transducer having multiple regions. The regions may provide respective power beams and measuring beams and methods are provided for estimating changes in efficiency while in use.

The principles and operation of an apparatus and method according to the present invention may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
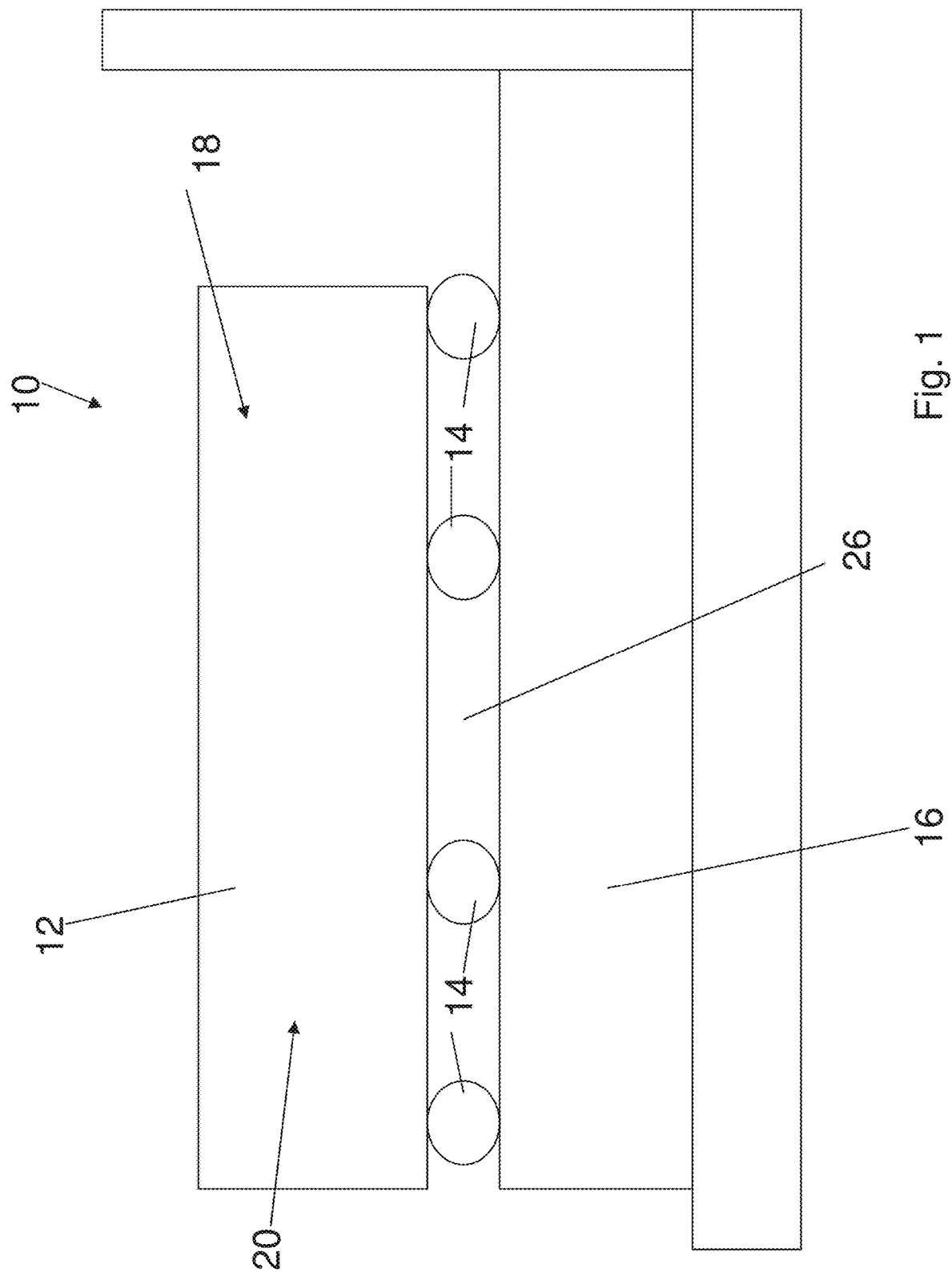

Reference is now made to FIG. 1, which is a simplified diagram showing a dual use ultrasonic transducer device 10 for combined sensing and power transmission. The transducer comprises a piezoelectric surface 12 of a piezoelectric element. The element is mounted using mounting points 14 to a printed circuit board 16. The combination of the PCB 16 and the mounting points 14 form a mounting.

The piezoelectric element is electrically connected to the printed circuit board. For example the mounting points may be comprised of conductive glue, or may include wire connections. The piezoelectric element is vibrated in use by the electrical input to transmit a beam and also vibrates in the presence of a beam to sense ultrasound echoes. Thus the mounting comprises damping for the piezoelectric element in order to manage the vibrations. The mounting may provide different levels of damping to various parts of the piezoelectric element so as to provide different regions on the surface which are distinguished by their different levels of damping. A highly damped region is good for sensing since an acoustic beam can be transmitted and the returning echo can be reliably read by a surface whose vibrations have already died down. On the other hand power transmission benefits from the vibrations mounting up so that an undamped surface may be considered, and on the contrary, a mounting that actually multiplies vibrations would be better.

Thus the embodiment of FIG. 1 may provide the two different levels of damping to two different parts of the surface, shown as 18 for the highly damped low power sensing region and 20 for the low damping high power transmission region, so that one part is optimized for power transmission and the other part is optimized for sensing. The two regions are connected using different electrodes so that their operation is kept separate.

The low damped, high power region 20 may be configured to provide the power transmission as a non-focused beam.

The non-focused beam may be provided from throughout the surface part 20, that is to say from throughout the body of the low damping high power region.

The power beam may provide a thermal effect to surrounding tissues, thus carrying out ablation. Different parts of the surrounding tissues may have different sensitivities to the non-focused power beam.

The sensing may provide imaging of the heating effect. Since, in the present embodiment, the surface doing the imaging is an extension of the surface providing the power beam, the sensing surface is necessarily correctly directed for sensing.

In an alternative embodiment, the same sensor surface may be used for both the power and imaging.

In a third embodiment different transducers may be placed on the device. Each transducer produces either a power beam or a measuring beam. Example configurations are shown below in FIGS. 8A and 8B.

The thermal effect that is used may comprise denaturation of collagen. The sensing may specifically involve detection of an increase in amplitude of the ultrasonic reflection over the transmitted beam, which increase in amplitude is an indicator of the denaturation of the collagen.

The power beam may be transmitted in bursts. The gaps in between the bursts may then be used to transmit separate sensing transmissions at lower power and allow detection without interference from the power beam.

The device is designed to be placed in a body lumen. The sensing region may detect the wall of the lumen, and this can be used to provide a signal that can be used in a control loop to control for distance to the lumen wall. The control loop can thus be used to ensure that the device does not touch the lumen wall.

The body lumen is generally liquid. The mounting, as discussed, includes gaps 26 between the contact points 14. The device may be designed so that gaps remain air filled even when the device is in the lumen. Thus the gaps 26 become air pockets which lie between the multiple contact points 14.

Figure 2:
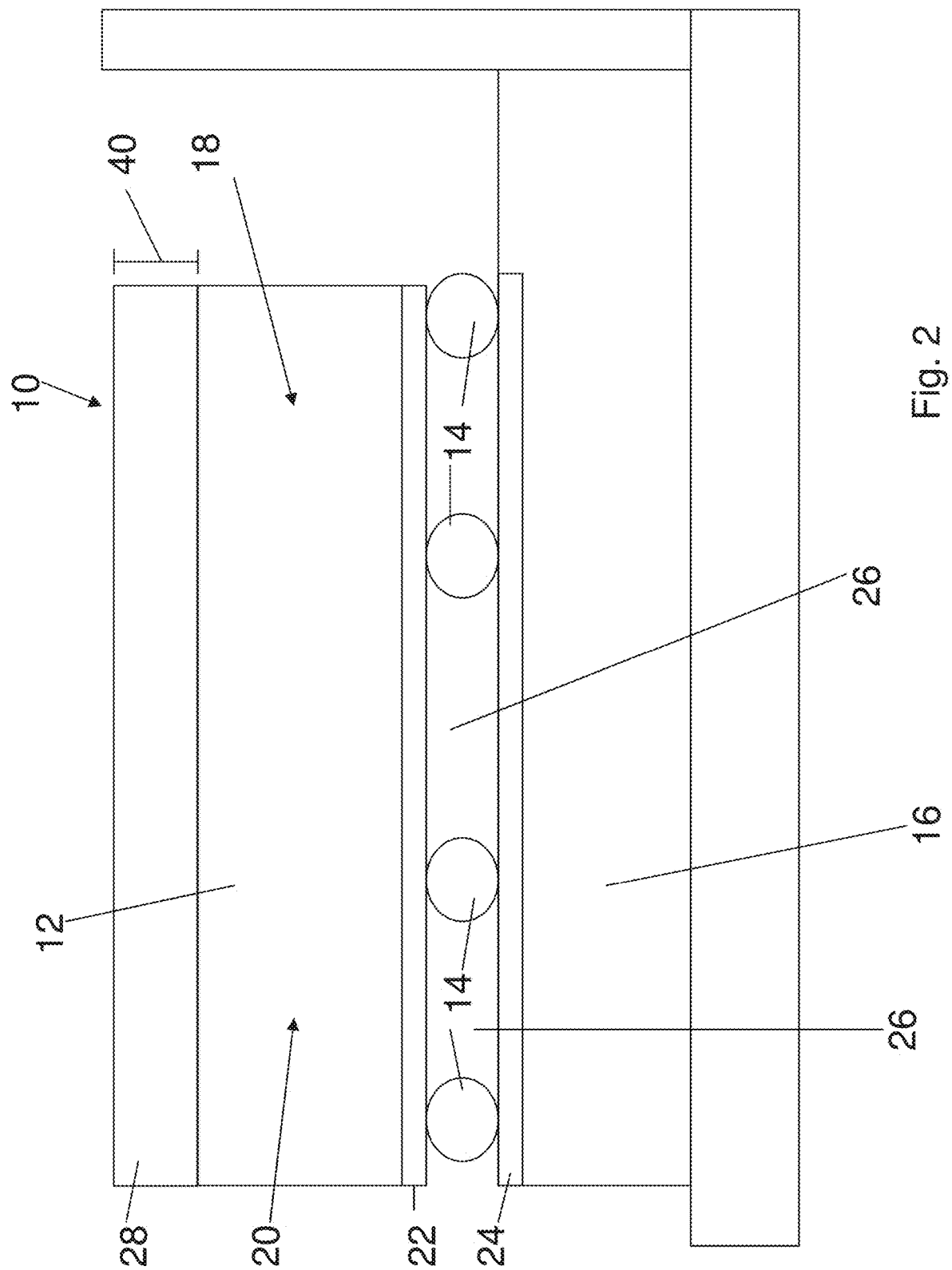

Reference is now made to FIG. 2 which is a variation of the device of FIG. 1.

As discussed, the air pocket may be maintained by surface tension. The mounting may be designed with a surface tension sufficient to maintain the air pocket when the device is immersed in liquid, and this may be due to the materials themselves, or, if not sufficient, then suitable coatings 22 and 24 may be applied.

In an embodiment, a matching layer 28, for acoustic impedance matching, may be placed on the piezoelectric surface 20. A suitable material for the matching layer is pyrolytic graphite, due to its combination of heat conducting ability and biological compatibility. Specifically pyrolytic graphite has little effect on platelets and thus does not increase the risk of clot formation.

In operation, electrical waves are applied to the acoustic surfaces 18 and 20, which causes the surfaces to vibrate. The surfaces have resonant and anti-resonant frequencies, and the working frequency at which the device is typically operated is an anti-resonance. The anti-resonance was found empirically to provide a highest efficiency in terms of a ratio of conversion of electrical energy to sound as opposed to conversion of electrical energy to heat.

Figure 3A:
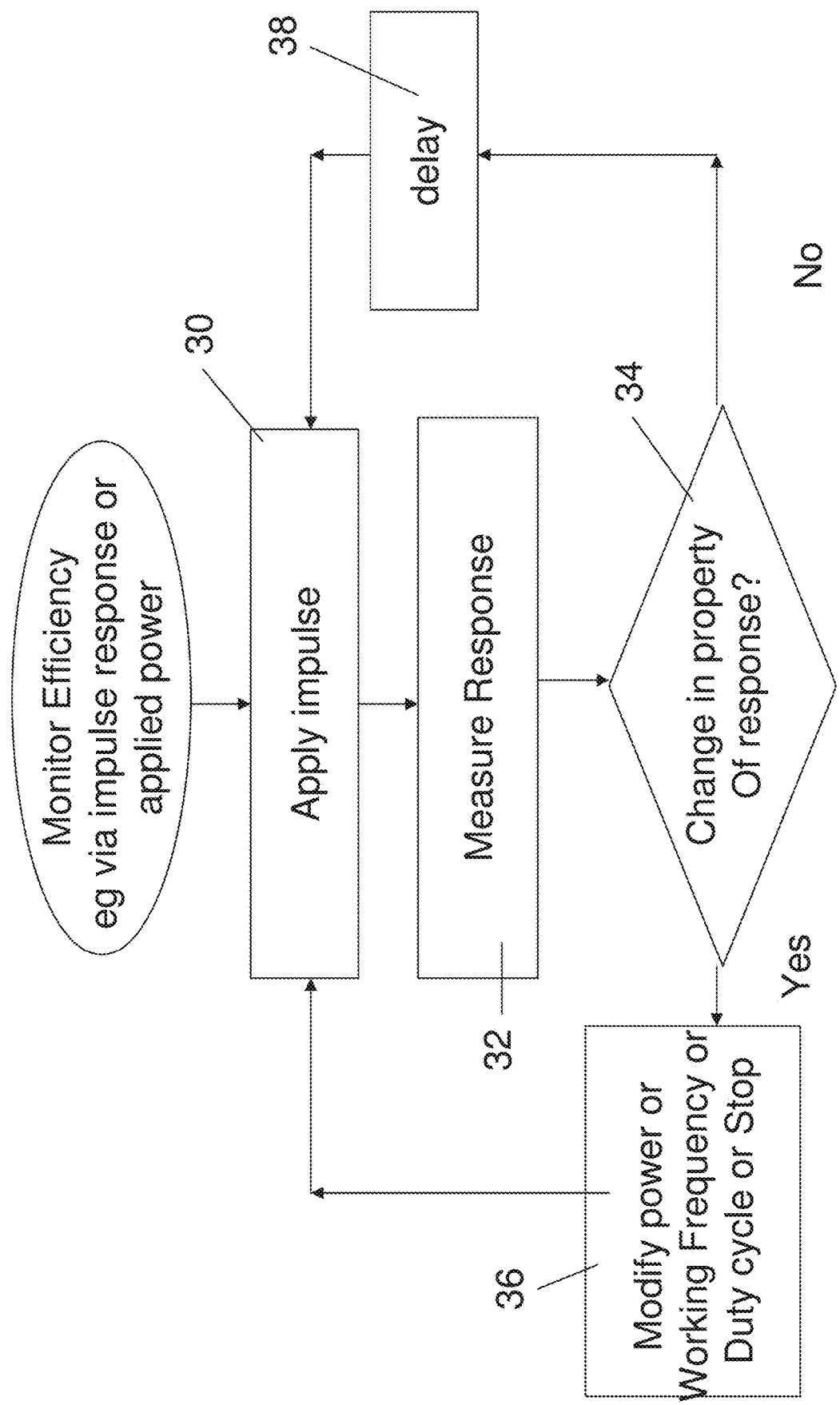

Reference is now made to FIG. 3A, which is a simplified flow diagram illustrating a method for monitoring operation of the transducer in order to control efficiency of the device of the present embodiments, or to control efficacy of the treatment, as will be explained hereinbelow. The device efficiency may change during use, typically leading to a danger of overheating. The problem is believed to lie with materials from the blood stream, particularly clots, getting attached to the device and changing the vibration dynamics. The anti-resonant frequency changes as a result but, unless this is detected, the device continues to work at the pre-defined working frequency. Thus the efficiency drops and the device heats up.

To help solve the above problem the present embodiments may provide a way of online testing of efficiency of the ultrasound transducer to detect changes in its efficiency. As mentioned above, the efficiency is a ratio between ultrasound energy and heat generated in the transducer. As shown in FIG. 3, the method involves applying an impulse to the ultrasound transducer, —box 30, and then measuring a response of the ultrasound transducer to the impulse, as shown in box 32. Changes in a property of the response may then be used in decision box 34 to infer changes in the efficiency of the device.

If such changes are detected then in box 36 an action is taken. The action may be stopping of the device. Alternatively it may involve changing the applied duty cycle and/or the applied power or alternatively the change may involve modifying the working frequency of the device. Subsequently, the efficiency is tested again so that the device can rapidly converge on a new efficient working frequency. If no changes are detected then a delay 38 may be introduced and the test repeated.

The test may be carried out continuously during use.

In the test, the changes in efficiency can be inferred from a change in a property of the impulse response, as shown in FIG. 3A. However alternatives for the test include scanning the device impedance against frequency, measuring the applied power and measuring the impedance during a pulse.

In the case of the impulse test, the property may be a shape or envelope of the measured response. Alternatively the property may be a duration of the measured response, typically the time the response falls to a predetermined minimal threshold.

The property may alternatively be an amplitude of the measured response, and as a further alternative the property may a damping factor, which is derived from the measured response.

As described above, the transducer device has both a resonance and an anti-resonance. Indeed the device may have several resonant frequencies and several anti-resonances formed from local maxima on the efficiency graph. The online testing may involve inferring changes in any of these maxima and minima and thus in either a resonance or an anti-resonance.

The efficiency testing is a form of test which can be carried out in situ in the liquid-filled body lumen since the impulse response can be monitored remotely via the contact points 14.

As an alternative, the impedance of the transducer device can be tested. A fall of say ten percent in the impedance can be taken as a signal to move the working frequency or to stop the treatment.

Reference is now made to FIG. 3B, which is a simplified diagram illustrating a more detailed control loop for the transducer device. In FIG. 3B, changes in power, current, voltage, impedance, and temperature are used together or as alternatives and changes are looked for. In the case of current, voltage, and impedance, changes of 10 percent are looked for. In the case of temperature a measurement in excess of 43 degrees is looked for. A pulse cycle using a given power P at a duty cycle of D% is applied and over excitation leads to the device stopping. Blood flow and acoustic feedback are also obtained.

Returning now to FIG. 2, and the ultrasonic transducer device, may have an acoustic matching layer 26 comprising pyrolytic graphite as discussed. The matching layer has a thickness 40, which is advantageously a quarter of a wavelength of the power beam transmitted by the ultrasonic transducer. As mentioned the working frequency could be the anti-resonance of the device so that the thickness 40 is a quarter of a wavelength of the working frequency.

Figure 4:
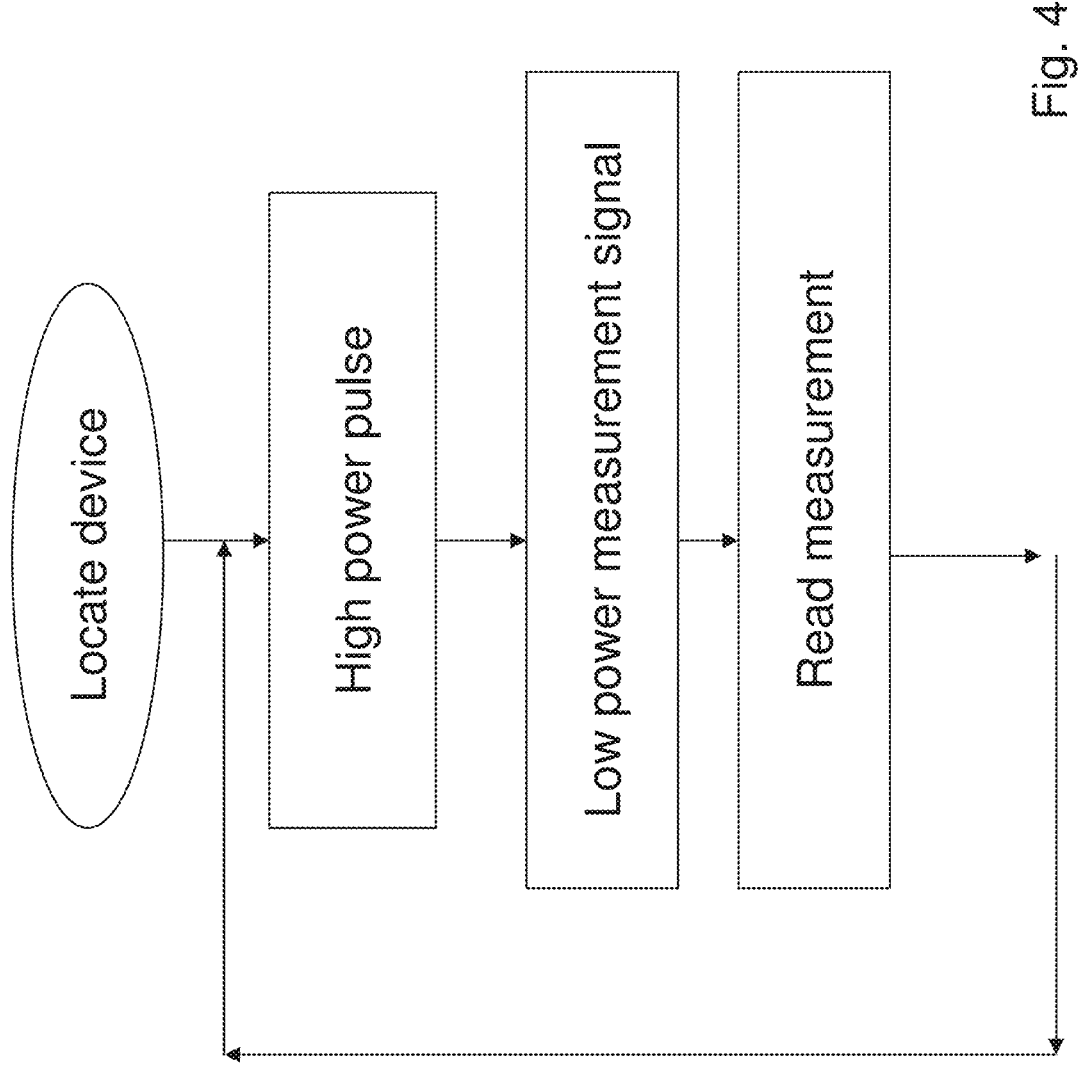

Reference is now made to FIG. 4, which illustrates a method of using an ultrasonic transducer of the present embodiments for simultaneous heating and monitoring of a target. The method comprises a box 50 for providing a relatively high power ultrasonic transmission in bursts for heating the target. The bursts have gaps, as discussed above, and the method uses the gaps to send relatively low power ultrasonic sensing transmissions—box 52—for monitoring the target. The measurements are then read—box 54. As discussed, the high power and low power beams may be provided from different parts of the same surface of a piezoelectric sensor which are differentially damped, at working frequencies which are anti-resonances of the transducer. Alternatively they may be provided from the same surface. Alternatively high power and low power beams may be provided from different transducers on the device.

The present embodiments are now considered in greater detail. The present embodiments relate generally to devices, parameters and methods for the treatment of tissue using ultrasonic waves in particular for heating, at a target area such as in the wall of a tube or cavity, located in the living body, The treatment may involve excitation using high power acoustic energy.

The ultrasonic effect is achieved in such a way that there is control over the heated target tissue volume and location. Preferably, a controlled volume of tissue between the ultrasonic element and the target tissue, is not treated. This distal effect may be achieved without the need of mechanical contact with the cavity walls.

Detailed application of the above includes the ability to cause moderate thermal damage within a controlled volume at the outer side of a cavity wall without damaging the inner side of the vessel, the inner side including different types of epithelium.

The treatment method may be applied by creating a gradient of different temperatures in the tissue by the combined effects of: heating the tissue with high power ultrasound and cooling of the tissue using conduction and convection. The convection could be of natural fluid, for example blood flow, or by artificial injection of cooling liquid, for example cold saline injection. Additional temperature effects that are widely elaborated in other sources may also simultaneously influence the temperature gradient, for example—capillary blood perfusion.

The heating control is performed by controlling the parameters of the ultrasonic field and the transmission protocol, including: transmission frequency, power, duration and duty cycle, as will be described in greater detail herein.

The treatment is controlled by feedback from the tissue using an echo received from the tissue during the treatment. Specifically, at high temperatures above 55° C. an irreversible change is created in the collagen fibers in the tissue; this change may be monitored using the ultrasonic echo from the tissue, which allows mapping of the damaged tissue area.

It is also possible to increase or\and to add effects by ejection of fluids into the treated area or at an upstream area in such a way that the ejected fluid is inserted into the vessel, typically through the vasa-vasorum or the adventitia lymph capillary.

Nevertheless, it is possible to control the flow in the vessel at different locations using different devices, for example a balloon opening in the vessel and again changing the treated effects in the tissue.

Typically, the ultrasonic transmission is applied at high power, high frequency and for more than one second. Heating of the tissue in the ultrasonic field is performed by absorption of the acoustic energy in a process of dissipation of mechanical energy. The absorption and influence of the energy on the tissue includes inter alia the following effects: a heating effect, a mechanical effect, a pressure effect, a sub-pressure and a cavitation effect.

Simultaneously with the transmission the cooling effect is achieved by liquid flow in the vessel or fluid present (for example urine, lymphatic liquid, bile) or liquid active ejection.

The present embodiments may provide the possibility of transmitting the energy without touching the cavity all. By not touching it is possible to increase protection for both the elements and the non target tissue by allowing fluid to flow on the cavity walls and on the transducer surface. The liquid provides for cooling. The present embodiments may also allow for easier operation by not restricting the transducer location.

The present embodiments may transmit a non-focused acoustic field to reach the target tissue. An advantage of not having to focus the field is that there is no need to control the tissue distance from the transducer. For example renal denervation may be carried out simply by allowing the catheter to transmit a wide, high power acoustic field from a nonspecific location in the artery to a distal nonspecific location of the renal nerve.

Embodiments of the invention may allow ejection of materials into the treated area or to an upstream area therefrom in a way that the materials are inserted into the vessel, say through the vasa-vasorum or the adventitia lymph capillary.

The embodiments described herein allow sampling of the voltage created on the ultrasonic element due to echoes from the tissue and processing the data in such a way that the treated tissue is monitored.

Echoe sampling and recording and or processing for measurement and monitoring can be performed simultaneously with the treatment. Such simultaneous treatment and analysis can increase the level of control of the treatment in real time and help ensure achievement of the desired results.

More specifically, the following information may be monitored from the echoes received within a vessel:
wall distance from the transducer,
vessel layer (media, adventitia, peri-adventitia) position,
thermal effect in the tissue location and
area of the thermal effect.

The data analysis method may include echo intensity, backscatter, spectral signature mapping, elastography, classification according to classification matrix of tissues, and the ultrasonic effect.

The control unit may use the above data and analysis for increasing the treatment, or reducing the treatment, or stopping the treatment, or providing indications regarding the treatment stage, or providing indications to stop or to continue the treatment.

A therapeutic catheter with an ultrasonic transducer may allow for transmission to the vessel from the inner side.

An ultrasonic transducer may be placed on the skin, with an internal catheter and transmission to the outer side of the cavity.

An endoscope system may include an ultrasonic element in its tip. The endoscope may be inserted through the skin and ultrasonic transmission may be provided to the outer side of the cavity.

The fluid control methods may include one or more of the following implementations:

A restrictor around the transducer. The implementation may involve: placing the transducer at a different location in the vessel, and controlling the flow;

A restrictor near the transducer. The implementation may again involve placing the transducer at a different location in the vessel, and controlling the flow;

A restrictor in front of (upstream of) the transducer. The method may involve blocking the flow upstream in order to load the vasa-vasorum with liquid and particles.

A restrictor past, that is downstream of, the transducer. The method may involve blocking the flow downstream of the transducer to allow drug delivery specifically to the treated area;

The restrictor may be one or more of the following: a balloon, a wire, nets, or a thin plastic sheet.

Manipulation of in the tissue reaction to the ultrasonic treatment is possible by:

Injecting vasoconstriction materials into the blood, and in this way reducing the perfusion and heat evacuation from the tissue, or injecting or evoking micro-bubbles and increasing the heating by increasing absorption of the ultrasonic energy, or the evoked micro-bubbles may be produced by use of an additional separate transducer.

Micro-bubble transportation through the cell membrane may be increased using the acoustic treatment, and may achieve a multiplied effect.

The tissue may be cooled before treatment in order to protect and or control the treated area and non-treated area.

Artificial opening of a minimal cavity surgery opening in the skin for insertion of the therapeutic catheter may be provided.

The ultrasonic field and/or the level of perfusion can be controlled and manipulated by influencing the body system in general.

Possible target tissues for the device include one or more of the following and their nearby tissues to douse cavities: arteries, veins, lymph vessels, intestine, esophagus, CNS, urine lumen, gall lumen, Stomach, and Tear Trough.

Applications for the above-described embodiments include the following:

Blood vessel wall pathology. For example for an atherosclerotic lesion;

Healthy blood vessel wall treatment;

Treatment of tissue near the blood vessel wall, for example renal denervation;

Treatment of tissue near the urine lumen wall, for example prostate treatment;

Treatment of tissue far from the urine lumen wall, for example prostate cancer.

More detailed examples for treatment and advantages using the present embodiments include phantom pain treatment in which, the target tissue is nerve tissue in the limbs. The catheter cavity may be located in a limb artery. The purpose of the treatment may be reducing phantom pain innervations by denerving the injured nerve.

A point to note is that the attenuation of the ultrasound field is smaller in the fatty tissue around the nerves than in the nerves themselves at the device frequencies. Furthermore the fatty tissue, due to its low heat conduction, isolates the heat created in the nerves. Such phenomena increase the selectiveness of the treatment.

An additional example of treatment is renal denervation.

In this treatment the target is the renal nerves. The catheter cavity is located in the renal artery. The purpose is to reduce pressure on the heart for high blood pressure patients. It is noted that the frequency, power and acoustic beam as per the data and results hereinbelow, treat the nerves without or with minimal damage to the artery. In addition, as in the previous example, the attenuation is smaller in the fatty tissue around the nerves than in the nerves themselves at the device frequencies, which increases the selectiveness of the treatment.

Possible treatment effects in the tissues can be one or more of the following:

Cell necrosis occurring in one or more of: lymphocytes, macrophages, smooth muscle cells, fibroblasts, endothelial cells, and neurons;

Reduced change in the tissue activity including: reducing smooth muscle function, reducing or blocking nerve activity, reducing or blocking the generation of the heart beat potential to the heart muscles;

Mechanical blocking of the vasa-vasorum or\ and the lymph capillary;

Mechanical changes in the collagen fibers, an increase or decrease in stiffness and reducing the maximal tension for tearing;

Biochemical changing in the tissues may include: reducing or preventing plate connection to collagen, and changes of material diffusion through the cell walls.

The device may be operated using typical parameters for acoustic transmission as follows:

Transmission frequency: 5-30 MHz;

imaging frequency 5-60 MHz;

Transmission intensity (SATA): up to 200 w/cm$^2$;

Transmission duration (total time): 1-120 seconds.

Figure 5:
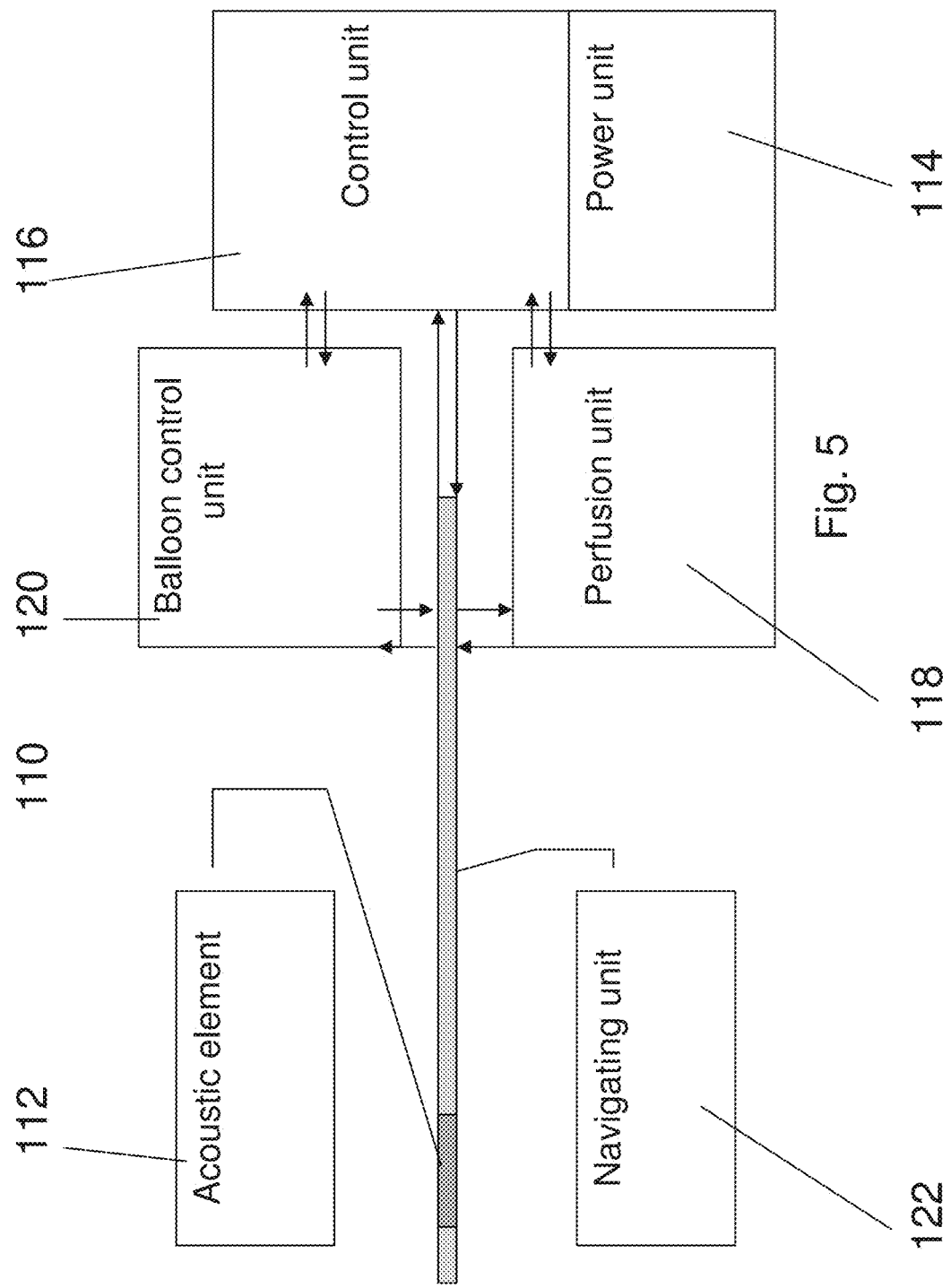

Reference is now made to FIG. 5, which is a simplified block diagram of a system according to an embodiment of the present invention. In FIG. 5, the system 110 may contain one or more of an acoustic transducer 112, a power supply unit 114, a control unit 116, a pumping or circulation unit, shown as perfusion unit 118, a balloon control unit 120, and a navigating shaft 122.

The navigating unit allows the acoustic element to navigate to the location or locations at which it is needed. The balloon control unit controls a balloon for supporting the lumen as needed. The perfusion unit provides injection substances as necessary.

Figure 6:
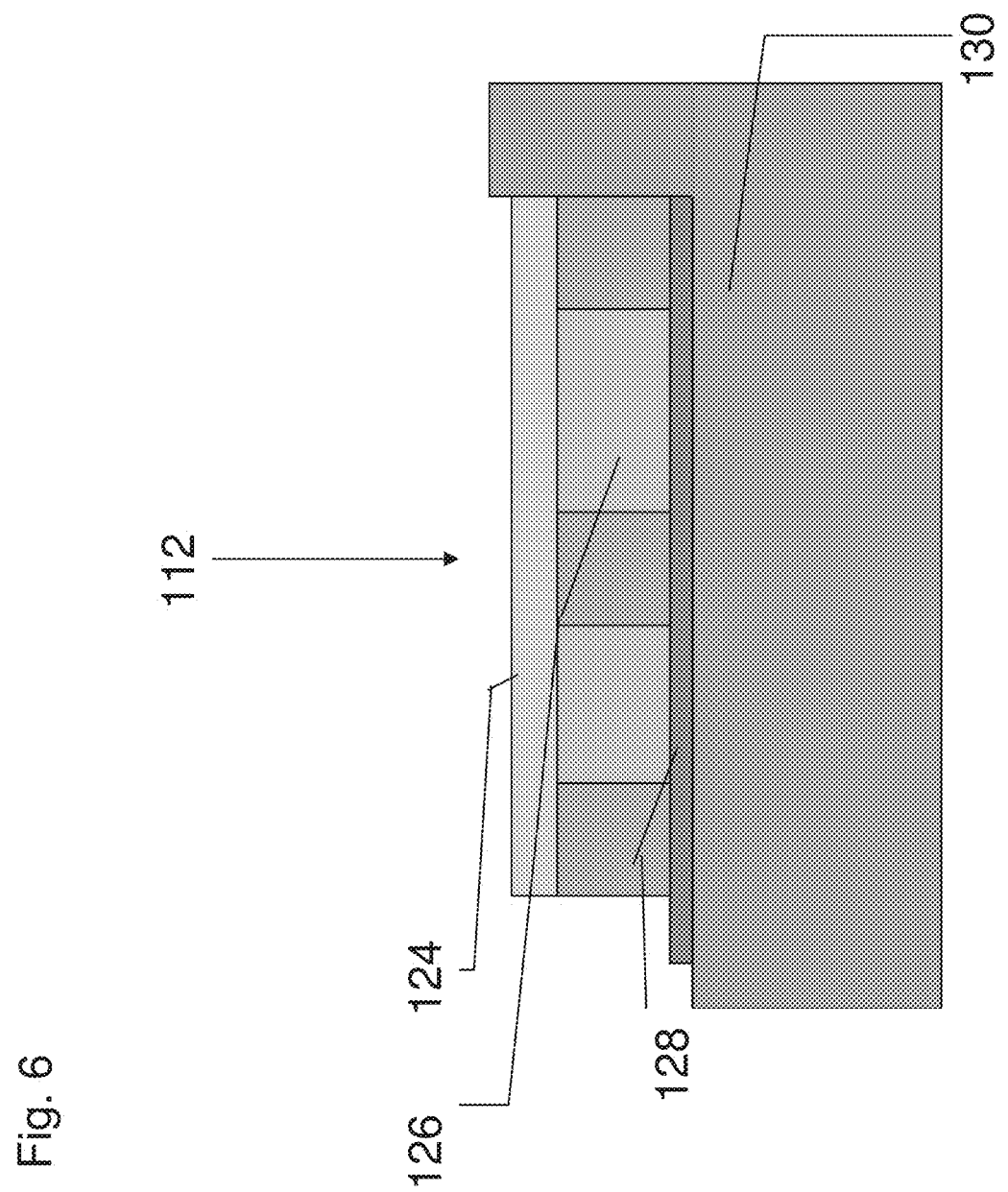

Reference is now made to FIG. 6, which is a schematic illustration of the acoustic element 112 of FIG. 1. The acoustic element 112, typically an ultrasonic element, includes a piezoelectric element 124 which converts electrical energy into an acoustic beam. The piezoelectric element is mounted on PCB board 126, for example via air gap 128. The PCB in turn is mounted on housing 130 which protects the acoustic element.

The ultrasonic elements transfer the energy to the target tissue, and may also be used as sensors for receiving reflections from the tissue.

The ultrasonic element may also be used as a jet evacuator of fluids for cooling or/and for drug delivery.

The ultrasonic element can be used as a microbubble evacuator.

The ultrasonic element typically includes one or more ultrasonic transducers including a piezoelectric material 24 or a MEMS element.

Electrodes may provide power to the transducer. The housing 30 protects the assembly, and an electrical connection may be provided between the electrodes and the catheter wires.

The transducer element 124 may, as mentioned by a piezo-electric elements or a MEMS element.

A PIEZO-electric transducer element may typically be made from PIEZO-electric material, for example: PZT ceramics, PIEZO-electric quartz.

Reference is now made to FIGS. 7A, 7B and 7C which illustrate designs for the ultrasonic element 112. FIG. 7A illustrates a series of shapes where the depth cross-section is rectangular as shown in element 132. The remaining elements in FIG. 7A are viewed from above. Element 134 is rectangular as seen from above. Element 136 is a hexagon. Element 138 is an irregular quadrilateral. Element 140 is a flattened circle. Element 142 is a trapezium. Element 144 is a bullet shape. Element 146 is a trapezium having a shorter dimension between its parallel sides than the trapezium of element 142. Element 148 is a comb shape having a narrow tooth at a first end followed by three wider teeth. Element 150 is a "W" shape, again with a narrow tooth projection at a first end.

FIG. 7B illustrates a closed ring shaped element 152 and an open ring shaped element 154.

FIG. 7C illustrates four variations on a cylindrical element. Element 156 is a filled cylinder. Element 58 is a cylinder with a removable sector. Element 160 is a hollow cylinder having an opening 161 in the lower wall, and element 162 is a hollow cylinder having an open part of the cylinder wall along its length.

In addition the element 112 may be spherical.

In embodiments the transducer described above does not necessarily include a focal point for the ultrasonic beam. As a result the beam can reach various targets without requiring a precise distance between the element and the target, as will be described in greater detail below.

Possible construction of the transducer may comprise regular coating methods for piezo elements, and coating materials including one or more of: silver, Ni, gold, copper, or carbon nano-tubes.

Additional coating of the electrodes may improve one or more of the following: the electric conductivity, the acoustic matching, the acoustic reflection or the acoustic amplification.

The additional coating may use any of a variety of materials including polymers, glass and metals.

The PIEZO-electric material may for example comprise: PIEZO-electric ceramics and/or PIEZO-electric quartz. An embodiment as discussed hereinbelow with cooling methods may allow the design to use high hardness ceramics, which have advantages of being of high efficiency, and being small and cheap.

MEMS—the acoustic element can also be implemented using MEMS.

More than one acoustic element can be implemented, for example:
a phased array matrix of elements;
a non-linear geometric array;
a matrix of elements each having different resonant frequencies Reference is now made to FIGS. 8A and 8B which illustrate examples for multi-elements transducers. FIG. 8A is a side view showing five piezoelectric elements 170 mounted on a curved PCB 172. FIG. 8B is a view from above showing two rows of piezoelectric elements 174 and 176.

The housing 130 can made from one or more of the following materials: metals, ceramics, PZT, PIEZO-electric ceramics, glass, polymers or carbons.

The housing may provide an angiogram directional projection for better placing of the element. The housing may further be shaped to provide focusing or to affect fluid flow within the lumen around the element.

The housing may be designed to provide relatively high heat transfer from the element in order to avoid overheating. Typically the heat conductance is a function of shape and of the material used, however standard cooling fins cannot be used in the blood stream as they may cause platelets to break, thus causing blood clots.

The housing can include acoustic damping materials, such as tungsten, or alternatively may be designed to provide an acoustic amplifying effect. As per the discussion above, typically some of the piezoelectric surface is damped and some is provided with acoustic amplification.

A drug delivery capsule may be provided to inject materials into the bloodstream as required by the procedure.

Reference is now made to FIG. 9, which illustrates an embodiment of a printed circuit board 16 for mounting of the acoustic transducer 12. The printed circuit board may include different thickness to provide the gaps for the air pockets referred to above.

The printed circuit may comprise materials such as hard polymers, flexible polymers, glass-fiber and carbon fiber. Alternatively, the printed circuit may be printed directly on the housing.

As discussed, connection to the acoustic element may use any of wire soldering, paste soldering process, conductive gluing and wire bonding. The connection is preferably both a good heat conductor and a good electrical conductor.

The circuit itself may include vias of copper or other metals for higher heat transfer. One or more printed materials may be provided on the board, including: copper, metals, polymers, and intermediate materials.

Coatings such as metals, PZT, chemical coatings, isolation coatings, hydrophilic coatings and hydrophobic coatings may be used on different parts of the PCB or housing.

The acoustic transducer may be connected to the control unit 116 using different kinds of wires including: coax wire, twisted pair, and fiber optic cable.

The acoustic transducer and the catheter may be coated with different coatings including: an isolation coating, a praline, NiSi, hydrophobic coating, hydrophilic coating, or any kind of biocompatible coating, As mentioned above, an air pocket may be maintained between the PCB and the peizoelectric element.

The acoustic isolation of the piezoelectric element and consequent increase in efficiency has been mentioned above. This advantage can be used for working in small cavities in order to improve the ability to heat the target volume without at the same time heating the transducer volume.

Air pockets may be formed by the use of trenches in the PCB structure as illustrated with reference to FIG. 9. or by providing a mounting as shown in FIG. 1 where a gap is defined between the ultrasonic elementelement and the PCB.

Hydrophobic coatings, including praline, may be used to enhance the surface tension effect in order to prevent the water medium from penetrating into the air volume, as mentioned in respect of FIG. 2.

The coating may cover the entire air bubble surrounding or part of it and prevent water from penetrating in.

It is noted that the air bubble does not need to be maintained indefinitely. It is sufficient that it is retained for the duration of the ultrasound procedure.

The ultrasonic element may use different anti-resonance values for the working frequency when available. For example one anti-resonance may be used for moderate heating of the tissue, another for power heating of the tissue and yet another for monitoring.

The device may be able to provide an injection jet to the tissue, may provide for increasing fluid flow under the element, say to improve cooling, may evoke micro-bubbles, and may monitor the heating effect and or any injection. The measurement system may include doppler analysis and the heat treatment may use focused or unfocused ultrasound.

In embodiments, the navigation unit 122 may allow the acoustic element to reach the desired location. The navigation unit may further have some auxiliary functions. For example it may deliver the power to the element from the control unit, record measurements from the element and even deliver the measurements to the control unit 116. The navigation unit may further be involved in heat absorption or transfer from the transducer to the ambient or to the surrounding liquids by providing an additional heat exchange surface extending from the catheter.

The navigation unit may also mechanically hold and place the ultrasonic elements in different locations and at different desired angles, as per FIG. 10. In FIG. 10 a ring configuration 180 may be used, or an angle configuration 182, or a cylindrical configuration 184 or a side configuration 186 or a front configuration 188, each in relation to the catheter.

In embodiments, the navigation unit may include an external navigated control unit. Close to the ultrasonic element, a placing unit may include a balloon, a placing wire or a net or the like.

A heat sink function may including cooling the ultrasonic unit using outside fluid including: blood, urine or CSF. The function may include increasing the heat evacuation by pumping fluid over or from the acoustic unit surface. The function may involve increasing the heat evacuation using internal or external heat conductive material, including: blood passivation coating, or printed coating, or may include increasing the heat evacuation using an internal or external heat conductive balloon.

Heat evacuation may be increased by using an internal or external heat conductive balloon with heat conduction material.

The control unit 116 may provide various kinds of closed loop control and indications on the treatments. The control unit may receive signals from echoes from the tissue. The echo may indicate the area and treatment effect, or the echo can indicate the distance from the cavity wall to the transducer device. The sensor may be a temperature sensor, which may indirectly sense the temperature of the transducer by measuring fluid that has just passed the sensor. The temperature may indicate the treatment efficiency, or efficiency of cooling of the cavity, or the cooling or heating of the transducer.

A power sensor can indicate the output treatment energy. A blood pressure sensor or other like sensors may be provided to indicate reaction to the treatment. A flow sensor can monitor fluid flow in the region of the treatment.

Closed loop effects which do not require the control unit may also be used, as known to the skilled person, for example a coating material on the transducer surface may be provided that attaches to particles or other materials that come from the treated tissue. The attachment may be used to control the ultrasonic process by making changes to the transducer frequency during operation.

Materials that can be inserted into the target tissue volume include restenosis prevention materials, for treatment of blood vessels, and materials that are used in drug eluting stents, such as sirolimus, and paclitaxel.

Other materials can be used, say in drug exuding balloons, and may include materials that are used for bio-degradable stents, anti-Inflammatory materials, medications that may be better presented locally to the tissue than systemically, anti-thrombotic materials, such as Heparin, Aspirin, Ticlopidine, and Clopidogrel, and materials that can cause damage or death to target tissues. Thus materials that can cause nerve death may be supplied for renal denervation.

Also, materials that may help in blocking of the tissue micro-circulation in heating, such as polymers that undergo cross linking, or soluble collagen, or material that may increase the ultrasonic heating of the tissue, such as micro-bubbles that cause higher energy absorption, may be used, or in the latter case generated on site.

Micro-bubble transportation through the cells membrane can be increased using the acoustic treatment, and achieve a multiplicative effect.

Also any kind of medication can be applied.

The transducer may be positioned on a catheter inside blood-vessels or blood cavities. Ultrasonic irradiation of the target tissue from inside the vessel lumen or cavity outwards may then be provided. Cooling of the piezoelectric element may be achieved by making the design sufficiently conductive and then using blood flow or flow of a fluid from an external source, such as saline that is irrigated into the blood vessel.

The transducer may be positioned on a catheter inside tissue canals or cavities of body fluids in the body, such as the urethra or urinary bladder, or in the spinal cord or brain ventricles (CNS fluid). Ultrasonic irradiation of the target tissue from inside the canal/cavity outwards may then be provided.

The transducer may alternatively be positioned on the tip of an endoscope or like device. The endoscope is inserted through a small hole in the skin, and the ultrasonic transducer is positioned on or near the target tissue.

For cooling, external irrigation is allowed to flow into the area of the treatment cavity. The endoscope tip may for example be positioned inside a balloon like device. The cooling fluid flows inside the balloon. The balloon is positioned next to the treatment tissue location. The ultrasonic transducer irradiates the target tissue through the balloon wall. Alternatively, the balloon may be positioned on the skin and not inserted through it. The treatment target may be near the skin.

The ultrasonic transducer may be positioned at a location that allows ultrasonic irradiation of the target tissue. Irrigation of required material in a liquid form may be provided into the blood vessels or lymphatic vessels that supply the perfusion or lymphatic capillaries of the target tissue volume, for example the artery vasa-vasorum.

The method may involve waiting a known time constant for the required material to reach the target tissue.

It is possible to add micro-bubbles to the fluid material in order to help with detection of presence of the material in the target tissue. Micro-bubbles may be detected using ultrasound and sub-harmonic imaging. Micro-bubbles may also improve heating of the target tissue under ultrasonic energy, due to higher absorption of the ultrasonic energy in the tissue volume where they are located.

Applying a thermal effect in the tissue may cause the capillaries to be blocked mechanically or by blood coagulation.

Ultrasound energy applies mechanical force on particles that are present in a liquid, when there is a difference in the acoustic impedance, which is a function of the density multiplied by the speed of sound, between the particles and the liquid. The applied force then pushes particles along the direction of the traveling ultrasonic waves. The mechanical force phenomenon can be used to ensure that required substances arrive at the treatment site.

The ultrasonic transducer may be positioned in a tissue liquid cavity such as a blood vessel, near the target tissue, while ensuring a liquid spacing between the target tissue and the ultrasonic transducer irradiating face. As mentioned above a control loop can be used to ensure that the transducer does not touch the vessel wall and damage epithelium cells.

The required material may be released into the tissue liquid cavity in a way that will cause some of the particles to enter the spacing between the target tissue and the ultrasonic transducer irradiating face. One way of doing this is to coat the face of the ultrasonic transducer with the required material, such that the operation of the ultrasonic transducer may cause particles of the required material to be released into the surrounding liquid.

Another possibility is to add micro-bubbles to the required material fluid in order to detect the material presence in the target tissue. Micro-bubbles may be detected using ultrasound and sub-harmonic imaging.

Yet another possibility is to activate the ultrasonic transducer so as to apply force on the required material particles to push the particles into the blood vessel wall near the ultrasonic transducer irradiating face, using the pushing effect mentioned above.

Another possibility is to apply the ultrasonic energy in short high power pulses with long separations between each pulse. This may apply mechanical force, as per the phenomenon discussed above, to the particles to push them into the tissue wall, without heating the tissue wall extensively.

A further possibility is that activation of the captured required material can be achieved by applying additional ultrasonic energy or some other kind of external energy such as a magnetic field on Ferro-electric particles, or an ultrasonic shock-wave to the particles The present embodiments may be used for the treatment of renal denervation. The transducer is simply positioned at 1, 2 or more treatment points, and there is no need for tip manipulation or accurate positioning. The total energizing duration may be between two seconds and two minutes. Real-time feedback of treatment progress may be provided. The advantages of ultrasonic treatment include directional, localized and remote target tissue effects with minimal damage to other closer tissues, possibly reducing pain, preservation of endothelium and elastic lamina structure and function, sot that there is no post treatment stenosis, or at least reduced post treatment stenosis, the avoidance of any mechanical contact on the blood vessel wall, and overall a more robust treatment effect due to real-time feedback.

The following table is a summary of currently contemplated clinical applications.

TABLE 1

Currently Contemplated Clinical Applications

| # | Application Name | Anatomy | Target |
|---|---|---|---|
| 1. | Renal sympathetic nerve modulation | Renal artery | Renal sympathetic nerves |
| 2. | Carotid sympathetic nerve modulation | Carotid artery | Carotid sympathetic nerves |
| 3. | Vagus sympathetic nerve modulation | Aorta | Vagus sympathetic nerve |
| 4. | Peripheral sympathetic nerve modulation | Peripheral blood vessels | Peripheral sympathetic nerves |
| 5. | Pain nerve modulation | Spinal cord cannel | Pain nerves |
| 6. | Restenosis decrease | All relevant arteries | Artery media and adventitia |
| 7. | Vulnerable plaque stabilization | All relevant arteries | Artery media and adventitia |
| 8. | Atherosclerosis passivation | All relevant arteries | Artery media and adventitia |
| 9. | Plaque volume decrease | All relevant arteries | Artery media and adventitia |
| 10. | Plaque thrombosis decrease | All relevant arteries | Artery media and adventitia |

TABLE 1-continued

Currently Contemplated Clinical Applications

| # | Application Name | Anatomy | Target |
|---|---|---|---|
| 11. | Tetanic limb muscle tonus decrease | Limb arteries or veins | Peripheral motor nerves |
| 12. | Atrial fibrillation prevention | Right atria | Pulmonary vain insertion |
| 13. | Cardiac arrhythmia prevention | Coronary arteries | Cardiac tissue pathology |
| 14. | Liver tumor necrosis | Inferior vena cava | Tumor |
| 15. | None-malignant prostate treatment | Urethra | Sick prostate tissue |
| 16. | Malignant prostate treatment | Urethra | Sick prostate tissue |
| 17. | Artery aneurysms stabilization | All relevant arteries | Aneurysm wall |
| 18. | Aortic aneurysms stabilization | Aorta | Aneurysm wall |
| 19. | Berry aneurysms sealing | Brain arteries | Aneurysm wall |
| 20. | Erectile dysfunction treatment | Internal Iliac | Artery media and adventitia |

Table 2 below summarizes embodiments of the technology and uses.

TABLE 2

Summary of Technology

1. Technology
  1.1. The ultrasonic transducer:
    1.1.1. Very small: 1.5X8 [mm]
    1.1.2. Very thin: 0.8 [mm]
    1.1.3. Very high ultrasonic intensity output:
      100 [W/cm$^2$] continuous
    1.1.4. Relatively high work frequencies: 10-25 [MHz].
    1.1.5. Biocompatible coating: Perylene
  1.2. The catheter
    1.2.1. Ultrasonic transducer cooling: vessel blood/liquid
      flow + catheter breading as heat sink
    1.2.2. Very flexible treatment tip: 10mm stiff length. (Pass
      through 8Fr "hokey-stick" guide catheter)
    1.2.3. Precise and easy torque following
    1.2.4. Standard 0.014 OTW
    1.2.5. Relatively small diameter: 6 Fr
  1.3. Distancing fixture
    1.3.1. Distancing transducer face from
      artery wall to prevent contact damage,
      with minimal mechanical forces on artery wall
2. Technology functionality
  2.1. Non-focused ultrasonic beam-like ultrasonic emission
    2.1.1. Simple anatomic
    2.1.2. Big treatment volume cross-section,
      the size of the transducer face (differing from
      focused ultrasound with small treatment volume)
    2.1.3. Relatively even spread of ultrasonic
      energy in beam cross-section (No need to precise
      anatomic positioning like in focused ultrasound)
  2.2. Treatment maneuverability and directionality
    2.2.1. Simple maneuvering with nearly 1:1 torquability.
    2.2.2. Simple treatment beam directivity
      feedback and control from standard
      angiograph (0, 90, 180, 270)
    2.2.3. No need for high operator skills
    2.2.4. No problem to use contrast agent during treatment
  2.3. Ultrasonic imaging using the
    unique transducer - Continuous
    measurement of distance to artery wall
    2.3.1. Treatment tip real positioning measurement
      (not possible only from angiography)
    2.3.2. Feedback to prevent high power operation
      of the transducer while touching the artery wall.
3. Tissue treatment
  3.1. Very fast treatment:
    3.1.1. Treatment duration of 30-5 sec per treatment point.

TABLE 2-continued

Summary of Technology 3.1.2. Possibly 4 treatment point per artery
   for renal denervation
3.2. Remote and localized effect
   3.2.1. Thermal effect volume in the tissue far
      from the transducer face: media, adventitia,
      Vasa-Vasorum, peri-adventitia, adventitia nerves, peri-
      adventitia nerves, peri-adventitia capillaries.
   3.2.2. Targeting tissues in varying distances
      from transducer face according to treatment
      parameters (not possible in most focused
      ultrasonic catheter designs)
   3.2.3. Possibility to apply thermal effect in
      tissues located 5mm from the lumen wall.
      Relevant for peripheral nerves blocking
      from peripheral arteries.
   3.2.4. Non targeted tissues on the beam path
      to the target tissue are not damaged.
   3.2.5. Importantly no damage to the endothelium,
      basal membrane and internal elastic lamina.
3.3. Tissue selectivity
   3.3.1. Highly selective remote thermal effect
      in nerve bundles that are covered with thick
      fat tissue. (most relevant to Renal Denervation
      in the Renal artery ostium)
3.4. Treatment special features for Renal Denervation
   3.4.1. Working very close to artery ostium: < 10 [mm]
   3.4.2. Working in short arteries: < 20 [mm]
   3.4.3. Working in small arteries: 4-3 [mm]
4. Safety
   4.1. The temperature of the blood that flows over
      the ultrasonic transducer does not go over 50 C
      while working in the maximal allowed operation
      intensity level 50 [W/cm^2].
   4.2. The temperature of the blood that flows over
      the ultrasonic transducer does not go over 43 C
      while working in the therapeutic operation intensity level 30
      [W/cm^2]. No need to add external cooling saline injection.
   4.3. The therapeutic treatment on the blood
      vessel wall is done with no
      mechanical contact with the vessel wall.
      No danger of damaging the vessel
      wall or disrupting any pathologies on the
      wall (Atherosclerosis plaques)
   4.4. Localized and controlled effect specifically
      in the targeted treatment volume.
      No non-controlled energy effects in
      other tissues (unlike in RF treatment).
   4.5. No blocking of the blood flow during the treatment
5. Possible implications
   5.1. Much less pain in treatment: fast
      blocking of nerves with no electric
      excitation of the target nerve and no
      effect on other nerves (In contrast with
      Unipolar RF treatment)

Reference is now made to FIGS. 11-16 which illustrate experimental results following use of the device.

FIG. 11 is a histology slide, using H&E stain, and showing the thermal effect in a pig carotid artery. The border of the thermal effect region in the tissue is marked with a dashed line and noted as "Thermal Damage". The setup used was an ultrasonic catheter from inside the blood vessel.

FIG. 12 is a histology slide, using H&E stain, and showing the thermal effect in a pig renal artery. The border of the thermal effect region in the tissue is marked with a dashed line and noted as "Thermal". A necrotic nerve inside the thermal effect region is marked with an arrow and "necrotic nerve" text. The setup involved an ultrasonic catheter from inside the blood vessel.

It is noted that the embodiments cause thermal damage in target tissues far from the lumen internal wall, while causing no thermal damage in the lumen wall internal layer.

Specifically in blood vessels it was shown that thermal damage was achieved in the adventitia or media layers, without causing any apparent damage in the intima layer, either the endothelium or the elastic lamina.

It is believed that the reason for this effect is that the ultrasonic energy heats the artery wall all along the beam, but the blood flow in the lumen cools the tissue that is close to the blood flow, thus the endothelium wall never heats sufficiently to be damaged. It is possible to find a setting for the treatment parameters so to cause heating above 55 C of the tissues far from the blood flow, while the temperature of the intima layer is kept below 55 C.

Exemplary results are shown in FIGS. 13 and 14 which are histology slides wherein analysis and marking of the thermal damage area to a pig Carotid Artery and a Pig Renal Artery respectively, is made by a trained pathologist.

Heating the adventitia or media can cause blocking of the flow inside the small capillaries (called Vasa-Vasorum) in the blood vessel media and adventitia, for example by mechanical crimping due to the shrinking of the connective tissue due to collagen denaturation, or due to thrombotic blocking by a thrombus that is formed in the Vasa-Vasorum because of the thermal damage (the blood flow in these vessels is very low so it can not cool the blood vessel).

FIG. 15 illustrates exemplary results for the above. A histology slide shows analysis and marking of the blocked Vasa-Vasorum with arrows placed by a trained pathologist in a pig Carotid Artery Vasa-Vasorum in the adventitia.

The treatment is intended to provide extensive thermal damage to specific target tissues while keeping nearby tissues undamaged.

It is believed that the ultrasonic energy absorption is different for different kinds of tissue and, and furthermore, the content of collagen fibers may differ.

Specifically it was shown that in nerve fibers that are wrapped by fat tissue, it is possible to cause extensive thermal damage to the nerve tissue, while there is no significant thermal damage in the fat tissue or/and to the tissue surrounding them.

FIG. 16 illustrates two histology slides with analysis and marking of the thermal damage, or nerve degeneration area made by a trained pathologist, for a pig renal artery, and nerves in adventitia.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. In addition, any priority document(s) of this application is/are hereby incorporated herein by reference in its/their entirety.

What is claimed is:

1. A method for online testing of efficiency or treatment efficacy of an ultrasound transducer to detect changes in said efficiency while said ultrasound transducer is positioned within a liquid filled body lumen during a treatment of tissue, said method comprising:
applying an electrical impulse to said ultrasound transducer;
measuring an electrical response of said ultrasound transducer to said electrical impulse;
inferring changes in said efficiency of said ultrasound transducer or changes in an efficacy of a treatment provided by said ultrasound transducer from said measured electrical response; and
modifying an operation of said transducer during said treatment based on the results of said inferring.

2. The method of claim 1, wherein said applying comprises applying said electrical impulse while said transducer is positioned within a blood filled blood vessel.

3. The method of claim 1, wherein said ultrasound transducer is positioned on a catheter for said treatment of tissue by emitting ultrasonic waves from said ultrasound transducer.

4. The method of claim 3, wherein said emitted ultrasonic waves are focused ultrasonic waves.

5. The method of claim 3, wherein said emitted ultrasonic waves are unfocused ultrasonic waves.

6. The method of claim 3, comprising positioning said catheter inside a blood vessel or blood cavity, prior to said applying.

7. The method of claim 3, comprising positioning said catheter inside said body lumen filled with said liquid, prior to said applying.

8. The method of claim 1, wherein said efficiency is a ratio between ultrasound energy and heat generated in said transducer.

9. The method of claim 1, wherein said inferring said changes in efficiency comprises inferring said changes in efficiency from at least one member of the group comprising: a shape of said measured electrical response; an envelope of said measured electrical response, a duration of said measured electrical response, and a damping factor of said measured electrical response.

10. The method of claim 1, wherein said inferring said changes in efficiency comprises inferring said changes in efficiency from amplitudes of said measured electrical response.

11. The method of claim 1, wherein said transducer has a resonance and an anti-resonance and wherein said inferring comprises inferring from a change in at least one of said resonance and said anti-resonance.

12. The method of claim 1, wherein said measuring comprises measuring an impedance of said transducer at a current working frequency, and wherein said inferring comprises inferring said changes in said efficiency from changes in said measured impedance.

13. The method of claim 1, comprising:
placing said transducer in said body lumen and in a flow of said liquid;
wherein said measuring comprises measuring temperature of said flowing liquid, and wherein said inferring comprises inferring a decrease in said efficiency or a change in said efficacy from an increase in said measured temperature.

14. The method of claim 13, wherein said measuring temperature comprises measuring temperature of said flowing liquid downstream of said transducer.

15. The method of claim 1, comprising placing said ultrasound transducer in a body lumen at a distance from a lumen wall and in a liquid flow, wherein said measuring comprises measuring liquid flow between the device and the wall, and wherein said inferring comprises inferring said changes in said efficiency or said efficacy based on changes in said flow measurements.

16. The method of claim 1, wherein said inferring comprises inferring a danger of overheating from said measured electrical response.

17. The method of claim 1, wherein said modifying comprises stopping the activity of said transducer based on the results of said inferring.

18. The method of claim 1, wherein said modifying comprises changing an applied duty cycle when activating said transducer based on the results of said inferring.

19. The method of claim 1, wherein said modifying comprises changing working power when activating said transducer based on the results of said inferring.

20. The method of claim 1, wherein said modifying comprises modifying the working frequency of said transducer based on the results of said inferring.

21. The method of claim 1, comprising repeating said applying, said measuring and said inferring during said treatment.

22. The method of claim 1, wherein said modifying comprises introducing a delay during said method for online testing.

23. The method of claim 1, comprising providing an indication based on said inferred changes.

24. The method of claim 1, wherein said treatment of tissue comprises heating the tissue of said body lumen using ultrasonic waves generated by said ultrasound transducer and cooling the tissue by said liquid in said body lumen.

25. The method of claim 1, wherein said measuring comprises measuring an impedance of said ultrasound transducer in response to said applied electrical impulse, and wherein said inferring comprises inferring changes in an efficiency of said ultrasound transducer from said measured changes in said impedance, and inferring changes in said treatment efficacy from said inferred changes in efficiency.

26. The method of claim 1, wherein said inferring comprises inferring changes in an efficiency of said ultrasound transducer from said measured changes in said electrical response, and inferring changes in said treatment efficacy from said inferred changes in efficiency.

27. The method of claim 26, wherein said modifying comprises modifying an operation of said transducer during said treatment to control said treatment efficacy based on the results of said inferring.

28. The method of claim 1, wherein said measuring comprises measuring changes in said electrical response of said ultrasound transducer to said electrical impulse.

* * * * *